(12) United States Patent
Cline et al.

(10) Patent No.: US 7,722,534 B2
(45) Date of Patent: May 25, 2010

(54) COMPACT FLUORESCENCE ENDOSCOPY VIDEO SYSTEM

(75) Inventors: Richard W Cline, Vancouver (CA); John J. P. Fengler, North Vancouver (CA); Joachim W. Boehm, North Vancouver (CA)

(73) Assignee: Novadaq Technologies, Inc., Mississauga, Ontario (CA)

( * ) Notice: Subject to any disclaimer, the term of this patent is extended or adjusted under 35 U.S.C. 154(b) by 131 days.

(21) Appl. No.: 11/969,974

(22) Filed: Jan. 7, 2008

(65) Prior Publication Data
US 2008/0228037 A1      Sep. 18, 2008

Related U.S. Application Data

(60) Division of application No. 10/899,648, filed on Jul. 26, 2004, now Pat. No. 7,341,557, which is a division of application No. 09/905,642, filed on Jul. 13, 2001, now Pat. No. 6,821,245, which is a continuation-in-part of application No. 09/615,965, filed on Jul. 14, 2000, now abandoned.

(51) Int. Cl.
    *A61B 1/04* (2006.01)
(52) U.S. Cl. .................. 600/160; 600/476; 600/181; 600/109
(58) Field of Classification Search .......... 600/109, 600/160, 178, 407, 476–478; 250/458.1
    See application file for complete search history.

(56) References Cited

U.S. PATENT DOCUMENTS

| 3,971,068 A | 7/1976 | Gerhardt et al. |
| 4,115,812 A | 9/1978 | Akatsu |

(Continued)

FOREIGN PATENT DOCUMENTS

DE      19608027      9/1996

(Continued)

OTHER PUBLICATIONS

Alfano et al., "Fluorescence spectra from cancerous and normal human breast and lung tissues," IEEE Journal of Quantum Electronics, QE-23(10):1806-1811, (1987).

(Continued)

*Primary Examiner*—John P Leubecker
(74) *Attorney, Agent, or Firm*—Rissman Hendricks & Oliverio, LLP

(57) ABSTRACT

A fluorescence endoscopy video system includes a multi-mode light source that produces light for color and fluorescence imaging modes. Light from the light source is transmitted through an endoscope to the tissue under observation. The system also includes a compact camera for color and fluorescence imaging. Images obtained through the endoscope are optically divided and projected onto one or more image sensors by a fixed beam splitter in the camera. The fixed beam splitter eliminates the need for inserting a movable mirror into the light path between the endoscope and the image sensors. Image signals from the camera are processed in the system processor/controller where a contrast enhancement function can be applied. The contrast enhancement function increases the color contrast between normal tissue and tissue suspicious for early cancer. Finally, the system also includes a calibration feature whereby the system performance can be maintained when used with different endoscopes.

15 Claims, 24 Drawing Sheets

U.S. PATENT DOCUMENTS

| | | |
|---|---|---|
| 4,149,190 A | 4/1979 | Wessler et al. |
| 4,200,801 A | 4/1980 | Schuresko |
| 4,378,571 A | 3/1983 | Handy |
| 4,532,918 A | 8/1985 | Wheeler |
| 4,556,057 A | 12/1985 | Hiruma et al. |
| 4,638,365 A | 1/1987 | Kato |
| 4,768,513 A | 9/1988 | Suzuki |
| 4,786,813 A | 11/1988 | Svanberg et al. |
| 4,821,117 A | 4/1989 | Sekiguchi |
| 4,837,625 A | 6/1989 | Souziech et al. |
| 4,930,516 A | 6/1990 | Alfano et al. |
| 4,951,135 A | 8/1990 | Sasagawa et al. |
| 4,954,897 A | 9/1990 | Ejima et al. |
| 5,007,408 A | 4/1991 | Ieoka |
| 5,034,888 A | 7/1991 | Uehara et al. |
| 5,134,662 A | 7/1992 | Bacus et al. |
| 5,165,079 A | 11/1992 | Schulz-Hennig |
| 5,214,503 A | 5/1993 | Chiu et al. |
| 5,225,883 A | 7/1993 | Carter et al. |
| 5,255,087 A | 10/1993 | Nakamura et al. |
| 5,365,057 A | 11/1994 | Morley et al. |
| 5,371,355 A | 12/1994 | Wodecki |
| 5,377,686 A | 1/1995 | O'Rourke et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,430,476 A | 7/1995 | Hafele et al. |
| 5,485,203 A | 1/1996 | Nakamura et al. |
| 5,507,287 A | 4/1996 | Palcic et al. |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,749,830 A | 5/1998 | Kaneko et al. |
| 5,772,580 A | 6/1998 | Utsui et al. |
| 5,827,190 A | 10/1998 | Palcic et al. |
| 5,833,617 A | 11/1998 | Hayashi |
| 5,986,271 A * | 11/1999 | Lazarev et al. ............ 250/458.1 |
| 5,986,642 A | 11/1999 | Lazarev et al. |
| 6,002,137 A | 12/1999 | Hayashi |
| 6,008,889 A | 12/1999 | Zeng et al. |
| 6,021,344 A | 2/2000 | Lui et al. |
| 6,059,720 A | 5/2000 | Furusawa et al. |
| 6,069,689 A | 5/2000 | Zeng et al. |
| 6,099,466 A | 8/2000 | Sano et al. |
| 6,120,435 A | 9/2000 | Eino |
| 6,148,227 A | 11/2000 | Wagnieres et al. |
| 6,212,425 B1 | 4/2001 | Irion et al. |
| 6,280,378 B1 | 8/2001 | Kazuhiro et al. |
| 6,293,911 B1 | 9/2001 | Imaizumi et al. |
| 6,364,829 B1 | 4/2002 | Fulghum |
| 6,422,994 B1 | 7/2002 | Kaneko et al. |
| 6,603,552 B1 | 8/2003 | Cline et al. |
| 7,043,291 B2 | 5/2006 | Sendai |

FOREIGN PATENT DOCUMENTS

| | | |
|---|---|---|
| EP | 0512965 | 11/1992 |
| EP | 0774865 | 5/1997 |
| EP | 0792618 | 9/1997 |
| FR | 2671405 | 7/1992 |
| JP | 60-246733 | 12/1985 |
| JP | 61-159936 | 7/1986 |
| JP | 07-155285 | 6/1995 |
| JP | 07-155286 | 6/1995 |
| JP | 07-155290 | 6/1995 |
| JP | 07-155291 | 6/1995 |
| JP | 07-155292 | 6/1995 |
| JP | 07-204156 | 8/1995 |
| JP | 07-222712 | 8/1995 |
| JP | 07-250804 | 10/1995 |
| JP | 07-250812 | 10/1995 |
| JP | 08-224208 | 9/1996 |
| JP | 08-224209 | 9/1996 |
| JP | 08-224210 | 9/1996 |
| JP | 08-224240 | 9/1996 |
| JP | 08-252218 | 10/1996 |
| JP | 10-127563 | 5/1998 |
| JP | 10-151104 | 6/1998 |
| JP | 10-201700 | 8/1998 |
| JP | 10-225426 | 8/1998 |
| JP | 10-243915 | 9/1998 |
| JP | 10-243920 | 9/1998 |
| JP | 10-308114 | 11/1998 |
| JP | 10-309281 | 11/1998 |
| JP | 10-309282 | 11/1998 |
| JP | 10-328129 | 12/1998 |
| JP | 11-089789 | 4/1999 |
| JP | 11-104059 | 4/1999 |
| JP | 11-104060 | 4/1999 |
| JP | 11-104061 | 4/1999 |
| JP | 11-104070 | 4/1999 |
| JP | 11-113839 | 4/1999 |
| JP | 11-155812 | 6/1999 |
| JP | 11-332819 | 12/1999 |
| WO | WO 95/26673 | 10/1995 |
| WO | WO 98/24360 | 6/1998 |
| WO | WO 99/01749 | 1/1999 |
| WO | WO 99/53832 | 10/1999 |
| WO | WO 00/42910 | 7/2000 |

OTHER PUBLICATIONS

Anderson-Engels et al., "Tissue diagnostics using laser induced fluorescence," Ber. Bunsenges Physical Chemistry, 93:335-342, (1989).

Hung et al., "Autofluorescence of normal and malignant bronchial tissue," Lasers in Surgery and Medicine, 11:99-105, (1991).

* cited by examiner

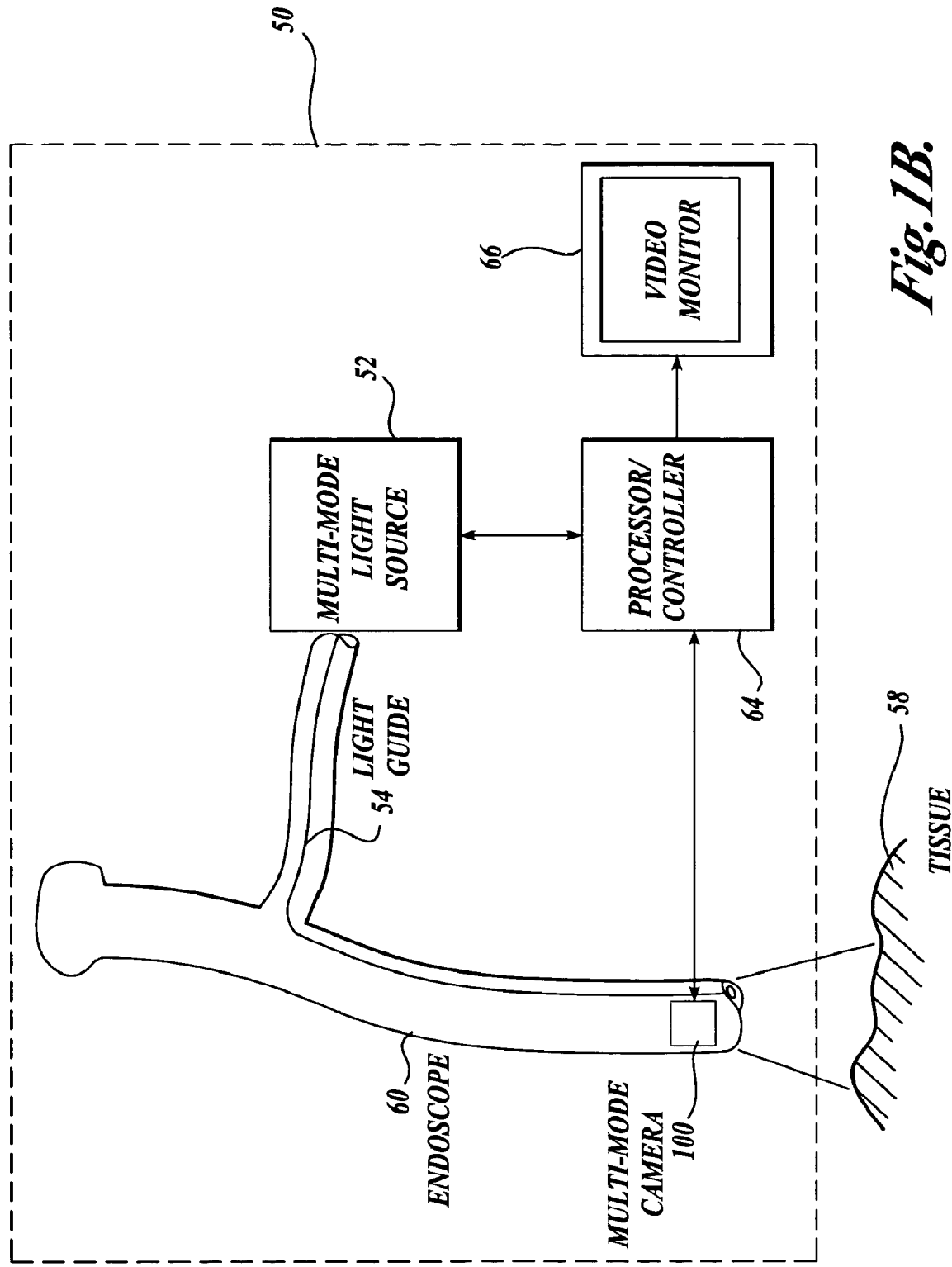

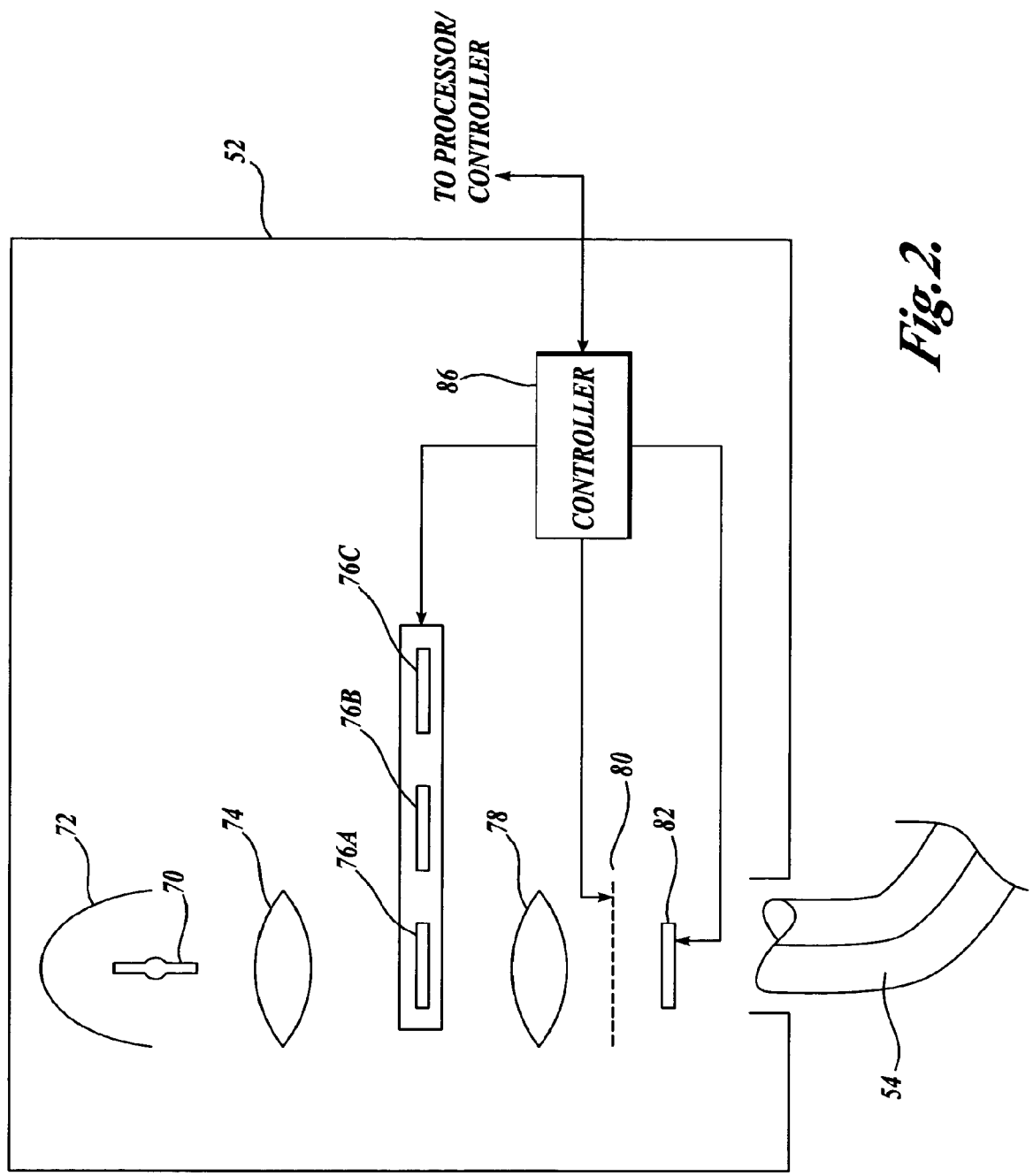

(A) PLATE (B) CUBE (C) PELCICLE (D) CUBE ASSEMBLY (E) CUSTOM PRISM

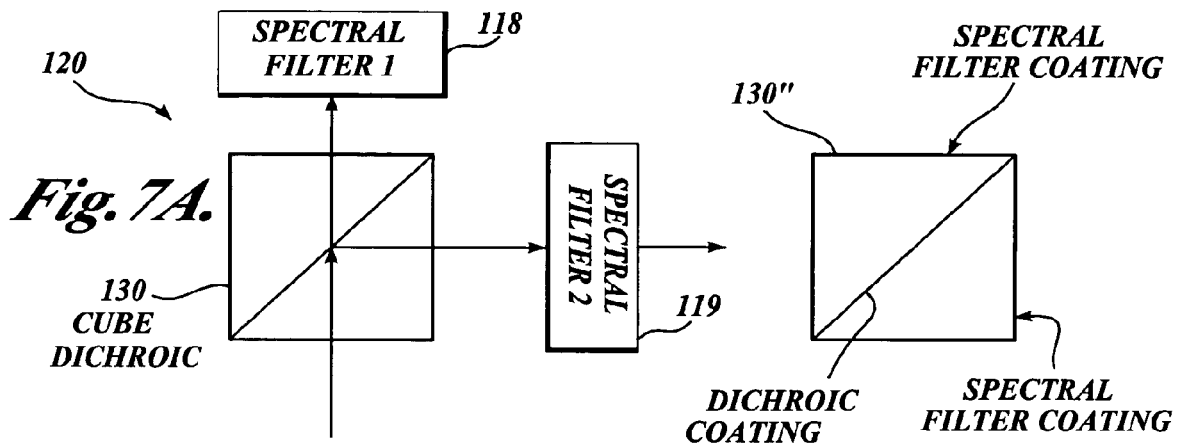
Fig. 7A.
Fig. 7B.
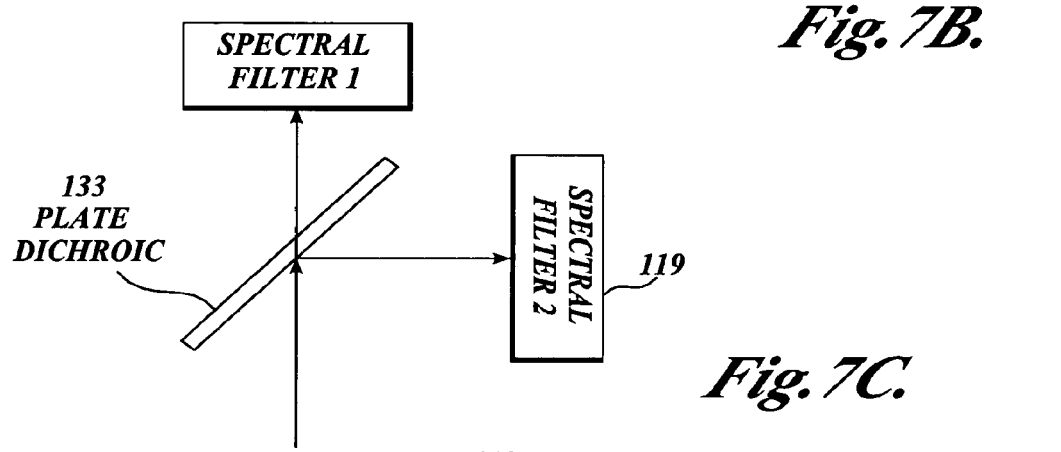
Fig. 7C.
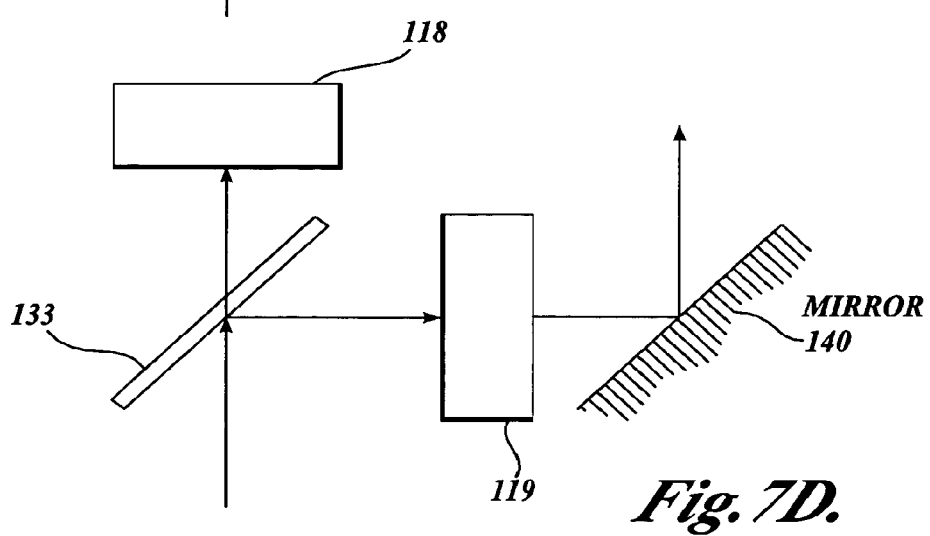
Fig. 7D.

370 < B < 460 nm
480 < G < 570 nm
590 < R < 750 nm

▨ = PREFERRED %
▩ = MAXIMUM ALLOWED %

OR $370 < B < 460$ nm
$480 < G < 570$ nm
$590 < R < 700$ nm
$700 < NIR < 850$ nm

▨ = PREFERRED %

▩ = MAXIMUM ALLOWED %

COMPACT FLUORESCENCE ENDOSCOPY VIDEO SYSTEM

This application is a divisional of Ser. No. 10/899,648, filed Jul. 26, 2004, now U.S. Pat. No. 7,341,557, which is a divisional of U.S. patent application Ser. No. 09/905,642, filed Jul. 13, 2001, now U.S. Pat. No. 6,821,245, which is a continuation-in-part of U.S. patent application Ser. No. 09/615,965, filed Jul. 14, 2000, now abandoned, the disclosures of all of which are incorporated herein by reference in their entirety as if fully set forth herein.

FIELD OF THE INVENTION

The present invention relates to medical imaging systems in general and, in particular, to fluorescence endoscopy video systems.

BACKGROUND OF THE INVENTION

Fluorescence endoscopy utilizes differences in the fluorescence response of normal tissue and tissue suspicious for early cancer as a tool in the detection and localization of such cancer. The fluorescing compounds or fluorophores that are excited during fluorescence endoscopy may be exogenously applied photoactive drugs that accumulate preferentially in suspicious tissues, or they may be the endogenous fluorophores that are present in all tissue. In the latter case, the fluorescence from the tissue is typically referred to as autofluorescence or native fluorescence. Tissue autofluorescence is typically due to fluorophores with absorption bands in the UV and blue portions of the visible spectrum and emission bands in the green to red portions of the visible spectrum. In tissue suspicious for early cancer, the green portion of the autofluorescence spectrum is significantly suppressed. Fluorescence endoscopy that is based on tissue autofluorescence utilizes this spectral difference to distinguish normal from suspicious tissue.

Since the concentration and/or quantum efficiency of the endogenous fluorophores in tissue is relatively low, the fluorescence emitted by these fluorophores is not typically visible to the naked eye. Fluorescence endoscopy is consequently performed by employing low light image sensors to acquire images of the fluorescing tissue through the endoscope. The images acquired by these sensors are most often encoded as video signals and displayed on a color video monitor. Representative fluorescence endoscopy video systems that image tissue autofluorescence are disclosed in U.S. Pat. No. 5,507,287, issued to Palcic et al.; U.S. Pat. No. 5,590,660, issued to MacAulay et al.; U.S. Pat. No. 5,827,190, issued to Palcic et al.; and U.S. Pat. No. 5,647,368, issued to Zeng et al. Each of these patents is assigned to Xillix Technologies Corp. of Richmond, British Columbia, Canada, the assignee of the present application. While the systems disclosed in the above-referenced patents are significant advances in the field of early cancer detection, improvements can be made.

These aforementioned systems are typically used in conjunction with an endoscope to which a camera containing low light sensors is attached or utilize a video endoscope with the camera located at the insertion end of the endoscope. In particular, it is desirable to reduce the size, cost, and weight of the camera described for these systems. Since fluorescence endoscopy is commonly performed as an adjunct to conventional white light endoscopy, it is also desirable for the system to be capable of acquiring both color and fluorescence images with the same camera and light source. It is also desirable to optimize such a fluorescence endoscopy video system to detect various types of cancer in different organs and to provide features so that it is easily calibrated for use with different types of endoscopes. It is also desirable that such a system be compatible for use with exogenously applied photoactive drugs. Finally, there is a need for a system in which the contrast between normal and suspicious tissue may be enhanced in the displayed fluorescence images.

SUMMARY OF THE INVENTION

A fluorescence endoscopy video system in accordance with the present invention includes:

an endoscopic light source that is capable of operating in multiple modes to produce either white light, fluorescence excitation light, or fluorescence excitation light with a reference reflectance light;

an endoscope including a light guide for transmitting light to the tissue under observation and either an imaging guide or compact camera for receiving light from the tissue under observation;

a compact camera that receives light from the image guide of an endoscope or directly from the tissue by virtue of being located in the insertion portion of the endoscope and is capable of operating in multiple imaging modes to acquire color or multichannel fluorescence and reflectance images. Images obtained are optically divided and projected onto one or more image sensors by a fixed beam splitter in the camera. One of the beams from the beam splitter is directed to an image sensor that acquires color images. The remaining beam is (or beams are) used alone or in conjunction with the first beam to acquire fluorescence and/or reflectance images;

an image processor and system controller digitize, process, and encode the image signals as a color video signal;

a contrast enhancement function may be present in the processor/controller. This function applies a non-unity gain factor to the processed reference image signal based on the relative intensity of the fluorescence/reflectance (or fluorescence/fluorescence) image signals;

a color video monitor displays the processed video images; and a color calibration mechanism allows the response of the system to be calibrated for optical characteristics of different endoscopes and/or other image signal path variables.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1B are block diagrams of fluorescence endoscopy video systems according to embodiments of the present invention;

FIG. 2 is a block diagram of a multimode light source in accordance with another aspect of the present invention;

FIGS. 7A-7D illustrate a number of spectral splitter and filter assembly configurations;

DETAILED DESCRIPTION OF THE PREFERRED EMBODIMENT

Figure 1A:
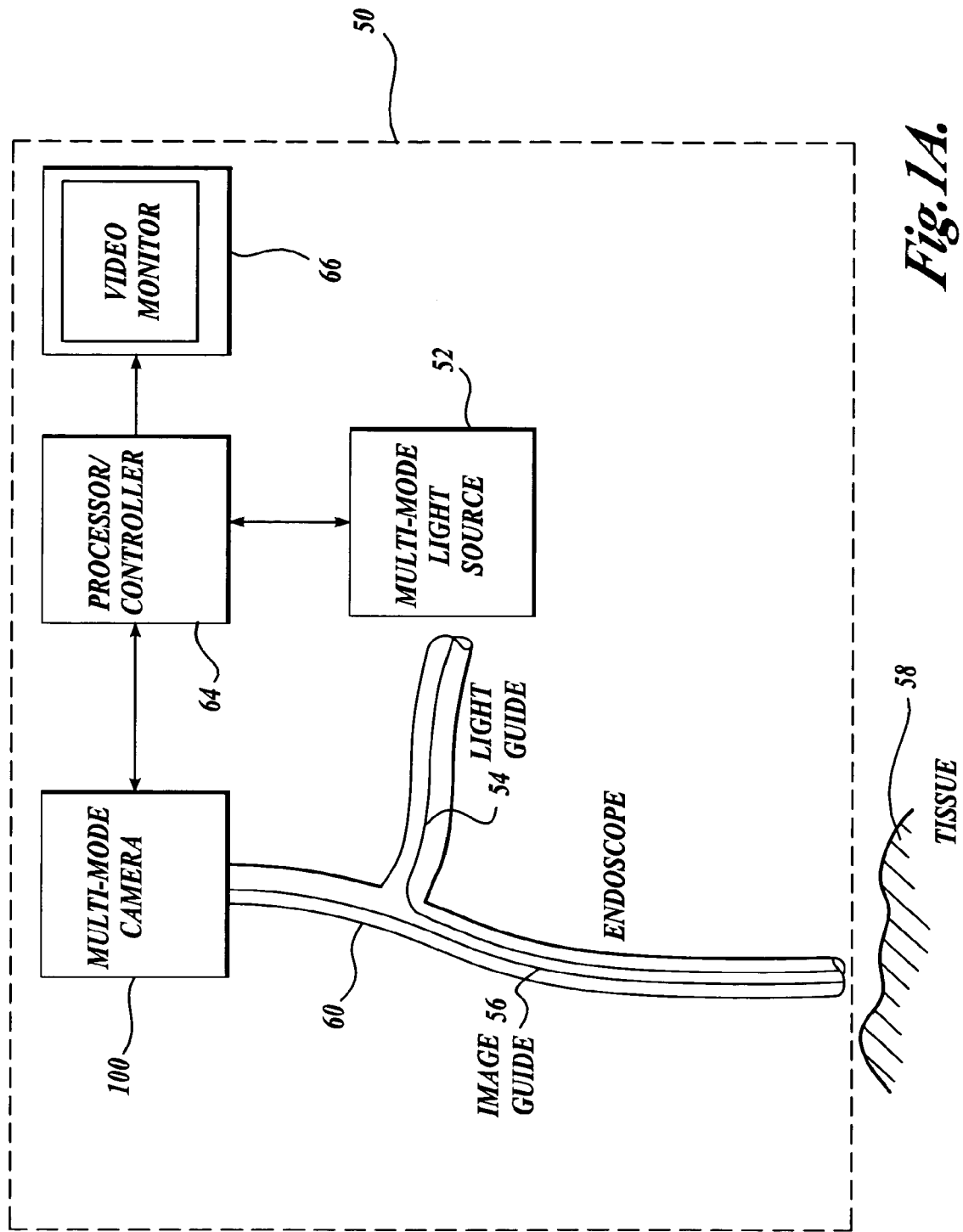

FIG. 1A is a block diagram of a fluorescence endoscopy video system 50 in accordance with a presently preferred embodiment of the present invention. The system includes a multimode light source 52 that generates a white light for obtaining color images. In a second mode of operation, the light source 52 produces an excitation light for inducing tissue autofluorescence. In a third mode of operation, the light source 52 produces an excitation light for inducing tissue autofluorescence and a reference reflectance light. The use of excitation light and excitation plus reflectance light for fluorescence/fluorescence and fluorescence/reflectance imaging modes will be described in further detail below. Light from the light source 52 is supplied to an illumination guide 54 of an endoscope 60, which then illuminates a tissue sample 58 that is to be imaged.

FIG. 2 shows the components of the light source 52 in greater detail. The light source 52 includes an arc lamp 70 that is surrounded by a reflector 72. In the preferred embodiment of the invention, the arc lamp 70 is a high pressure mercury arc lamp (such as the Osram VIP R 120P24). Alternatively, other arc lamps or broadband light sources may be used, but a high pressure mercury lamp is currently preferred for its combination of high blue light output, reasonably flat white light spectrum, and small arc size.

The light from the arc lamp 70 is coupled to a light guide 54 of an endoscope 60 through appropriate optics 74, 76, and 78 for light collection, spectral filtering and focusing respectively. The light from the arc lamp is spectrally filtered by one of a number of optical filters 76A, 76B, 76C . . . that operate to pass or reject desired wavelengths of light in accordance with the operating mode of the system. For color imaging, optical filter 76A eliminates any spectral peaks and modifies the color temperature of the light produced by the arc lamp 70. The transmission characteristics of the light source filters 76B, 76C . . . for fluorescence/reflectance and fluorescence/fluorescence imaging modes, respectively, are discussed in conjunction with the characteristics of the camera filters 118, 119A, 119B . . . below.

An intensity control 80 that adjusts the amount of light transmitted along the light path is positioned at an appropriate location between the arc lamp 70 and the endoscope light guide 54 and controls the amount of light coupled to the light guide 54. In addition, a shutter mechanism 82 may be positioned in the same optical path in order to block any of the light from the lamp from reaching the light guide. A controller 86 operates an actuator that moves the filters 76A, 76B, or 76C into and out of the light path. The controller 86 also controls the position of the intensity control 80 and the operation of the shutter mechanism 82.

As shown in FIG. 1A, the system also includes a multimode camera 100. The light that is collected from the tissue by the endoscope 60 is transmitted through an image guide 56 and is projected into the multimode camera 100. Because fluorescence endoscopy is generally used as an adjunct to white light endoscopy, each of the various embodiments of the camera described below may be used both for color and fluorescence/reflectance and/or fluorescence/fluorescence imaging.

FIG. 1B is a block diagram of an alternative fluorescence endoscopy video system 50, which differs from that shown in FIG. 1A, in that the multimode camera 100 is located at the insertion end of the endoscope and the endoscope does not contain image guide 56. With these differences, the resulting endoscope 60 can be characterized as a fluorescence video endoscope, similar to video endoscopes currently on the market (such as the Olympus CF-240L) in utility, but with the additional ability to be utilized for both color and fluorescence/reflectance and/or fluorescence/fluorescence imaging.

Other than the location of the multimode camera 100 at the insertion end of the endoscope and the lack of an endoscope image guide 56, the system of FIG. 1B is identical to that shown in FIG. 1A. The various embodiments of the camera described below lend themselves to implementation in a fluorescence video endoscope due to their compactness.

In this alternative system, the multimode camera 100 directly collects the light emitted by the tissue. By locating the camera at the insertion end of the endoscope, the inherent advantages of a video endoscope can be obtained: namely, the light available to form an image and the image resolution are improved compared to the case when the image is transmitted outside the body through an endoscope imaging guide.

Figure 3A:
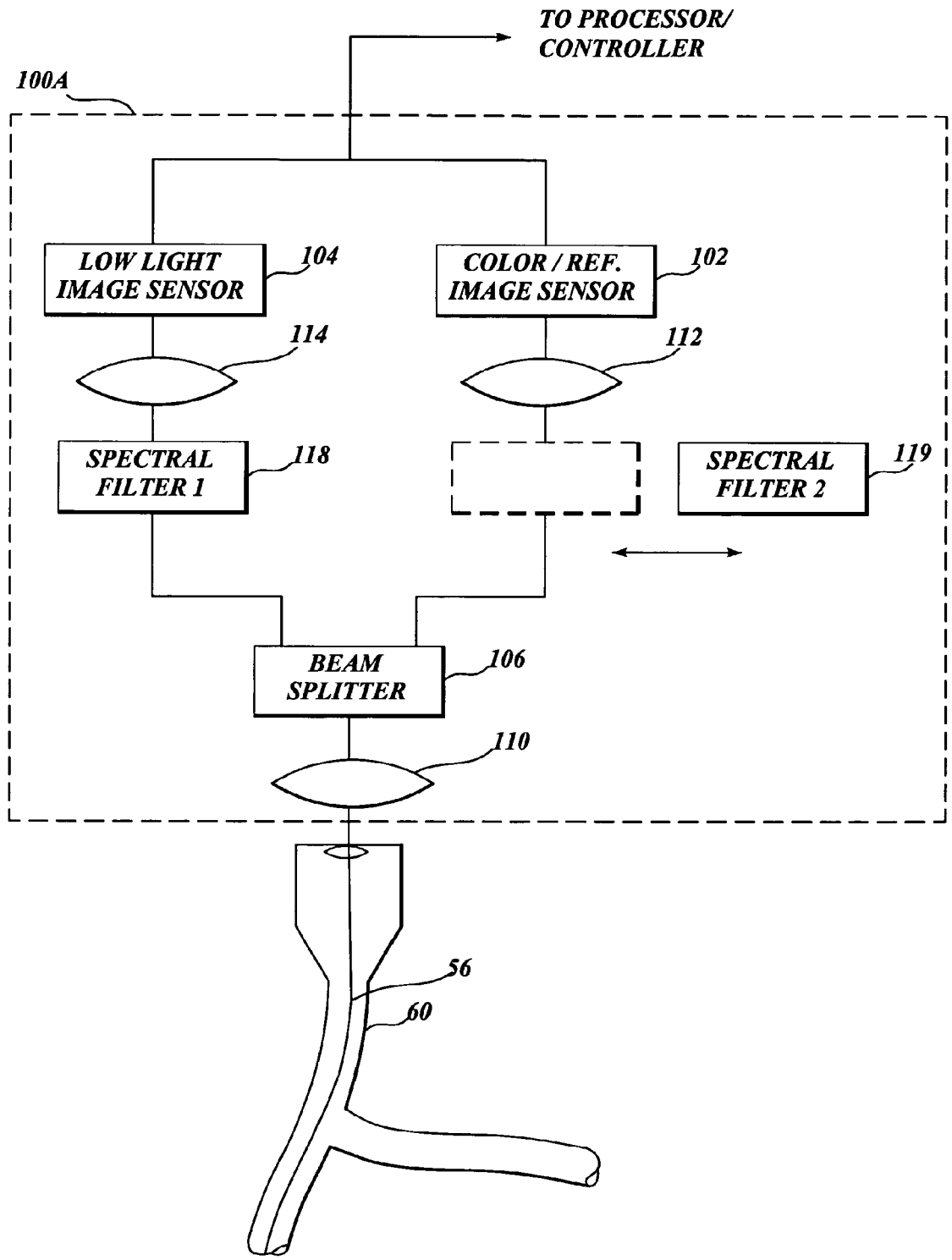
FIGS. 3A-3C illustrate a preferred embodiment of the camera that can acquire color, fluorescence/reflectance, and/or fluorescence/fluorescence images according to the present invention with optional placement for collimation and imaging optics.

In the first embodiment, shown in FIG. 3A, a camera 100A receives light from the image guide 56 of an endoscope 60 and directs the light towards a color image sensor 102 and a low light image sensor 104. In prior art camera designs, light is typically directed to either of the two image sensors 102 or 104 with a movable mirror that is selectively inserted into the optical path. Such a mirror must be carefully constructed so that it moves within tight tolerances. This adds greatly to the complexity and cost of the camera. The need to maintain these tight tolerances throughout the lifetime of the system also decreases the camera's reliability.

Figure 4A:
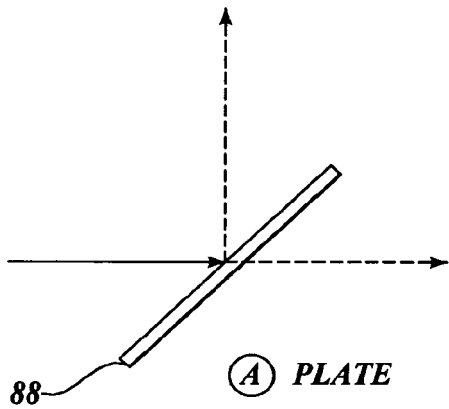
FIGS. 4A-4E illustrate a number of camera beam splitter configurations.
Figure 4B:
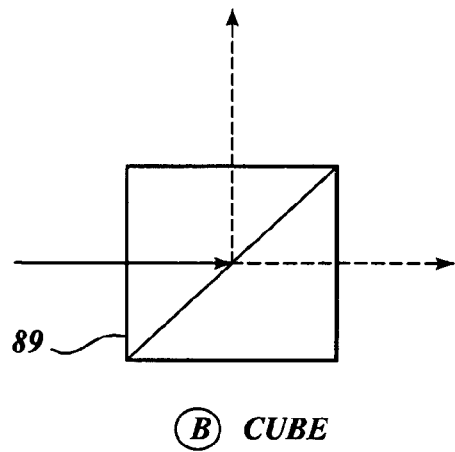
Figure 4C:
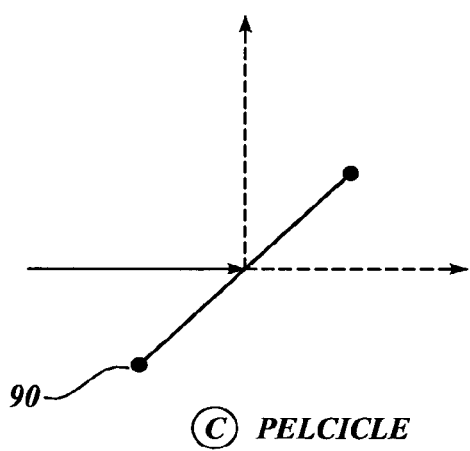

The camera 100A, according to the preferred embodiment of the present invention, replaces the moving mirror with a fixed optical beam splitter 106 that splits the incoming light into two beams. The light beam is split such that a smaller proportion of the light received from the endoscope 60 is directed towards the color image sensor 102 and a larger proportion of the incoming light is directed towards the low light image sensor 104. In this embodiment, the beam splitter may be a standard commercially available single plate 88, single cube 89, or single pellicle design 90, as shown in FIGS. 4A-4C. It should be noted that, if the optical path between the endoscope 60 and image sensors contains an uneven number of reflections (e.g., such as from a single component beam splitter), the image projected onto the sensor will be left-to-right inverted. The orientation of such images will need to be corrected by image processing.

Figure 4D:
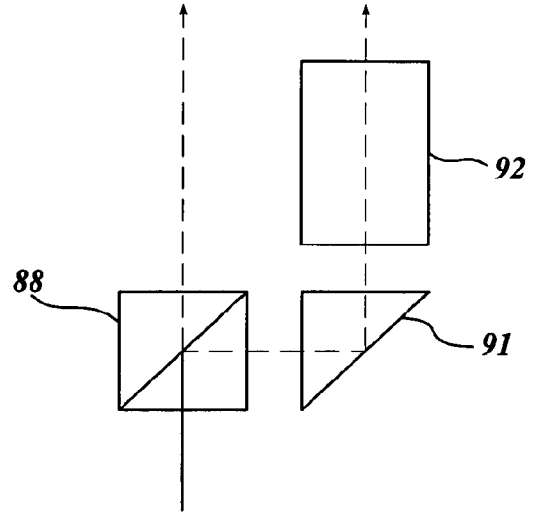
Figure 4E:
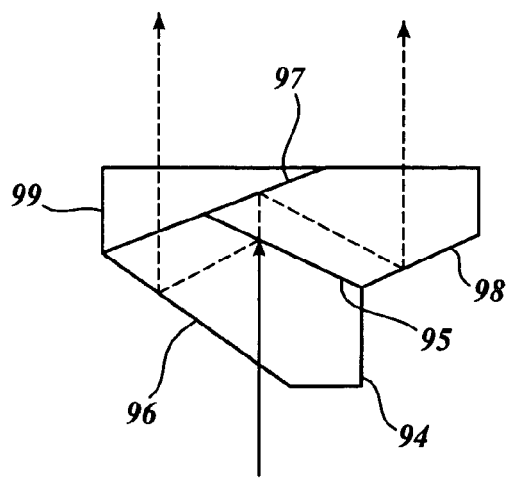

In some instances, it is desirable that the light split by the splitter 106 be projected in the same image plane. Therefore, the optical beam splitter 106 may be a combination of simple components or a custom prism design as shown in FIGS. 4D-4E. The cube assembly shown in FIG. 4D is an example of standard, commercially available glass components (beam splitter cube 89, right angle prism 91, and simple glass block 92) that have been combined into an assembly. Because the path of the light that passes through the right angle prism 91 is longer than that which passes through the beam splitter cube 89, for cases in which noncollimated light is being split by the splitter 106, the glass block 92 is positioned behind the right angle prism 91 to compensate for the different path lengths such that both beams are focused in the same image plane.

The custom prism shown in FIG. 4E is comprised of three prisms. A first partially-mirrored surface 95 on a first prism directs a portion of the incoming light toward a fully reflective surface 96 on the first prism. Light reflected off the surface 96 passes through a second prism 99. Light passing through the partially-mirrored surface 95 is reflected off fully reflective surfaces 97 and 98 of a third prism. The optical path length of the beam that is reflected by the partially mirrored surface 95 is the same as the optical path of the light that passes through the partially-mirrored surface 95.

The custom prism shown in FIG. 4E has the advantage that it is more compact than the cube assembly and that it provides a continuous surface from which the image sensor(s) may be located. In both of these versions of the beam splitter, the two paths for the split image contain an even number of reflections and are optically equivalent in length. In the case of an optical imaging configuration as described in FIG. 3C below, this allows both images to be projected into the same image plane (e.g., such as would be required if both images were imaged with a single image sensor).

In FIG. 3A, light collimating optics 110 are positioned between the endoscope 60 and beam splitter 106, and imaging optics 112 and 114 are positioned immediately preceding the color image sensor 102 and the low light image sensor 104, respectively. In an alternative optical configuration shown in FIG. 3B, the collimating optics 110 have been eliminated. Such a configuration is preferable to that in FIG. 3A, if the light beam from the endoscope 60 is already collimated.

Figure 3B:
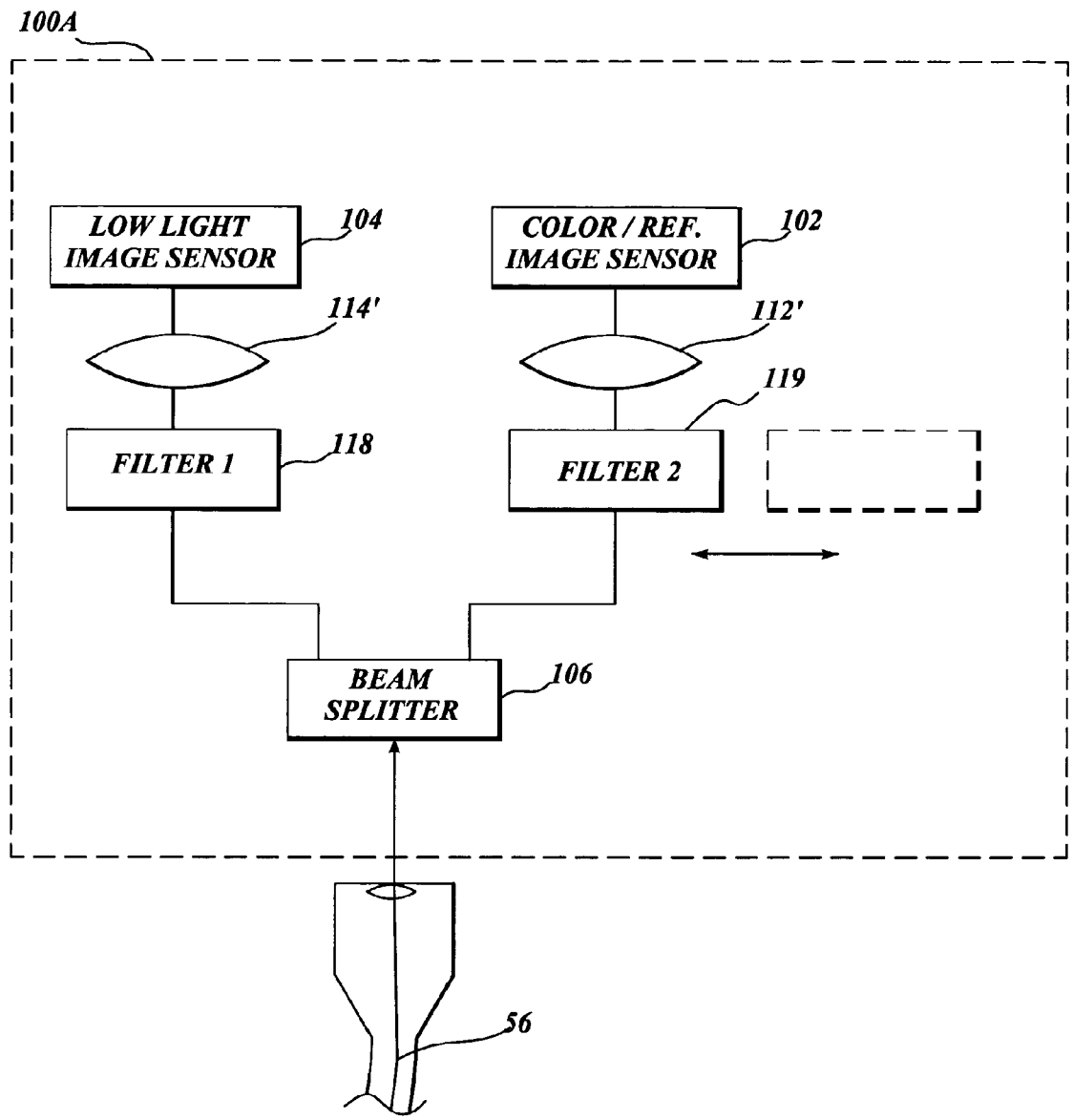
Figure 3C:
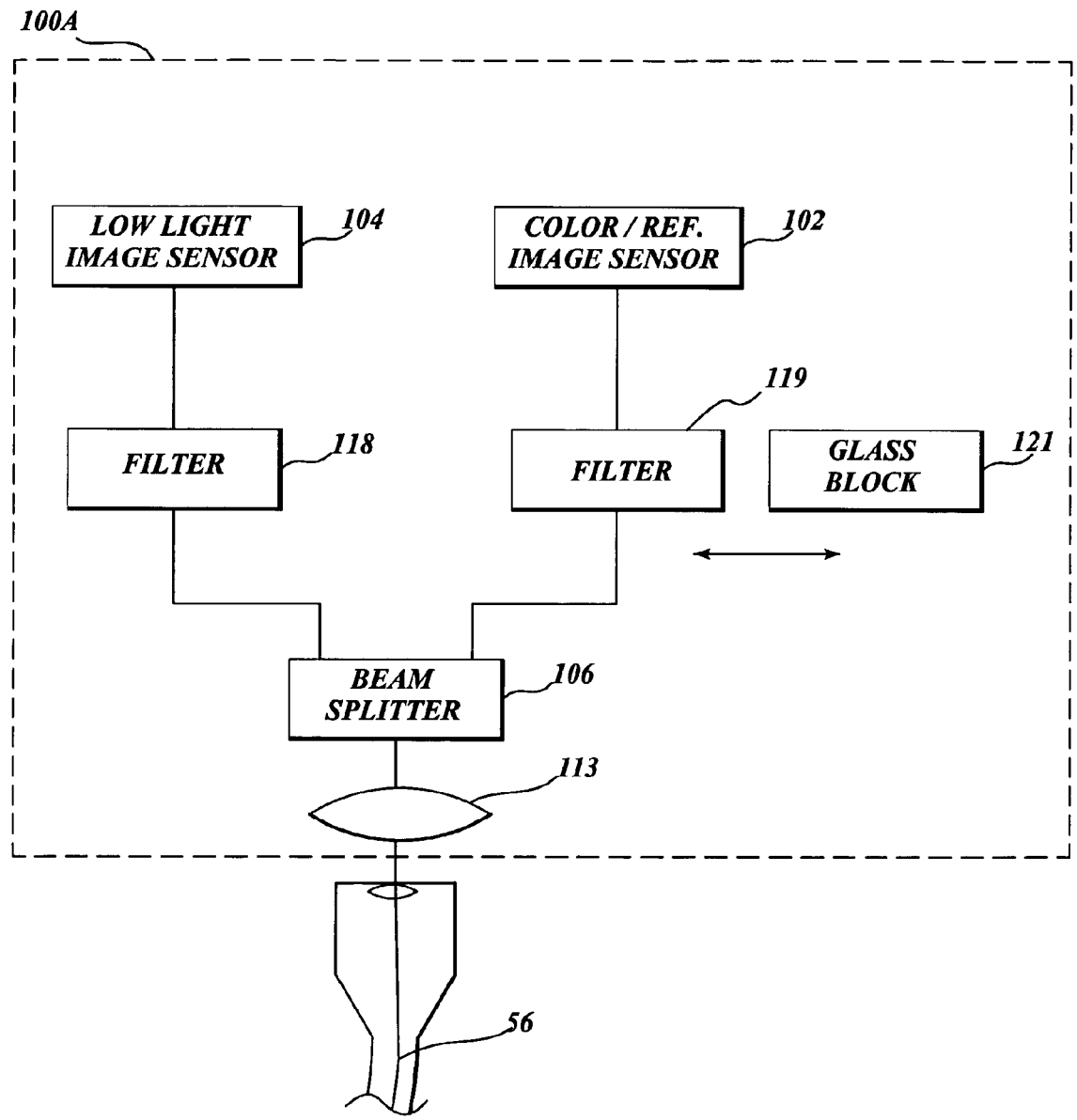

The presently preferred configuration of the camera 100A is shown in FIG. 3C. In this embodiment, the collimating optics 110 have been eliminated and replaced with a single set of imaging optics 113 located between the endoscope 60 and beam splitter 106. The advantage of this configuration is that all imaging is performed and controlled by the same imaging optics 113. Such a configuration requires all beam paths to have the same optical path length, however, and this restriction must be considered in the design of the beam splitter 106 and a pair of spectral filters 118 and 119 that are located in the path to the image sensors 102 and 104. Glass block 121 is inserted into the optical path when spectral filter 119 is removed. In addition, the fact that these optical elements are located in a converging beam path must be considered in specifying these elements and in the design of the imaging optics 113. All of the options for the collimating and imaging optics described above, and their attendant benefits and drawbacks, also apply to the subsequent descriptions of camera embodiments represented in FIGS. 5, 6, 8, and 10.

As shown in FIGS. 3A-3C, a spectral filter 118 is located in the optical path between the beam splitter 106 and the low light image sensor 104. Alternatively, the spectral filter 118 may be incorporated as an element of the beam splitter 106.

A second spectral filter 119 is positioned so that it can be moved into and out of the optical path between the beam splitter 106 and the color image sensor 102. For the case in which beam splitting is occurring in a noncollimated beam path, when filter 119 is moved out of position, a glass block 121 with the same optical path length as filter 119 is moved into position between the beam splitter 106 and the color image sensor 102 to maintain a constant optical path length. Alternatively, this insertable spectral filter 119 and glass block 121 (if required) may be incorporated elsewhere in the optical path between the endoscope 60 and the color image sensor 102. Moving a filter into and out of an optical path can be done with a simple mechanism as there are no stringent mechanical and optical requirements like those for moving a mirror.

The low light image sensor 104 preferably comprises a monochrome charge coupled device (CCD), monochrome charge coupled device with charge carrier multiplication (such as the Texas Instruments TC253 or the Marconi Technologies CCD65), intensified charge coupled device (ICCD), charge injection device (CID), charge modulation device (CMD), complementary metal oxide semiconductor image sensor (CMOS) or electron beam charge coupled device (EB-CCD) type of sensor. The color image sensor 102 is preferably a color CCD, a color CCD with charge carrier multiplication, a three-CCD color image sensor assembly with charge carrier multiplication, a three-CCD color image sensor assembly, a color CMOS image sensor, or a three-CMOS color image sensor assembly.

As shown in FIG. 1A, the system also includes a processor/controller 64 and a video monitor 66. The processor/controller 64 receives the transduced image signals from the camera 100 and digitizes and processes these signals. The processing of these signals may include the application of certain contrast enhancement algorithms described below. The processed signals are then encoded in a video format and displayed on a color video monitor 66.

Based on operator input, the processor/controller 64 also provides control functions for the fluorescence endoscopy video system. These control functions include providing control signals that
    control the camera gain in all imaging modes;
    coordinate the imaging modes of the camera and light source;

provide a light level control signal for the light source, and provide control signals for any image data management systems that may be used to record and archive image data.

The reason that two separate images in different wavebands are acquired in the fluorescence/reflectance and fluorescence/fluorescence modes of fluorescence endoscopy video systems described herein will now be explained. It is known that the intensity of the autofluorescence in certain wavebands changes as tissues become increasingly abnormal (i.e., as they progress to frank cancer). When acquiring images within such a waveband of autofluorescence, however, it is not easy to distinguish between those changes in the signal strength that are due to pathology and those that are due to imaging geometry and shadows. A second fluorescence image or a reflected light image, acquired in a waveband in which the image signal is not significantly affected by tissue pathology, may be utilized as a reference signal with which the signal strength of the first fluorescence image can be "normalized."

This normalization may be performed by assigning each of the two image signals a different display color, e.g., by supplying the image signals to different color inputs of a color video monitor. When displayed on a color video monitor, the two images are effectively combined to form a single image, the combined color of which represents the relative strengths of the signals from the two images. Since the color of the combined image is independent of the absolute strength of the separate image signals, the color will not change as a result of changes in the distance or angle of the endoscope 60 to the tissue sample 58 or other imaging geometry factors. If, however, there is a change in the shape of the autofluorescence spectrum of the observed tissue that gives rise to a change in the relative strength of the two image signals, such a change will be represented as a change in the color of the displayed image.

The mixture of colors with which normal tissue and tissue suspicious for early cancer are displayed depends on the gain applied to each of the two separate image signals. There is an optimal gain ratio for which tissue suspicious for early cancer in a fluorescence image will appear as a distinctly different color than normal tissue. This gain ratio is said to provide the operator with the best combination of sensitivity (ability to detect suspect tissue) and specificity (ability to discriminate correctly). If the gain applied to the reference image signal is too high compared to the gain applied to the fluorescence image signal, the number of tissue areas that appears suspicious but whose pathology turns out to be normal, increases. Conversely, if the relative gain applied to the reference image signal is too low, sensitivity decreases and suspect tissue will appear like normal tissue. For optimal system performance, therefore, the ratio of the gains applied to the image signals must be maintained at all times.

In vivo spectroscopy has been used to determine which differences in tissue autofluorescence and reflectance spectra have a pathological basis. The properties of these spectra determine the particular wavebands of autofluorescence and reflected light required for the fluorescence/reflectance imaging mode, or the particular two wavebands of autofluorescence required for fluorescence/fluorescence imaging mode. Since the properties of the spectra depend on the tissue type, the wavelengths of the important autofluorescence band(s) may depend on the tissue being imaged and the location within those tissues. The specifications of the optical filters described below are a consequence of these spectral characteristics, and are chosen to be optimal for the tissues to be imaged.

The operation of the preferred embodiment of the fluorescence endoscopy video system will now be described. The camera 100 shown in FIG. 1 is capable of color, fluorescence/reflectance, and fluorescence/fluorescence imaging modes. In the color imaging mode, the processor/controller 64 provides a control signal to the multimode light source 52 that it should be in white light mode. The light source 52 selects and positions the appropriate optical filter 76A into the optical path between the arc lamp 70 and the endoscope light guide 54. This filter 76A removes any spectral peaks and adjusts the color temperature of the light produced by the arc lamp 70. The filtered light from the light source 52 is projected into the endoscope light guide 54 and is transmitted to the tip of the endoscope 60 to illuminate the tissue 58.

The processor/controller 64 also ensures that the camera is in the correct imaging mode to avoid damage to the sensitive low light image sensor 104. In the case where the low light image sensor 104 is an ICCD, for example, the voltage across the photocathode is set to zero. The light reflected by the tissue 58 is collected by the endoscope image guide 56 and is projected through the camera beam splitter 106 onto the color image sensor 102. Spectral filter 119 is removed from the optical path during this imaging mode and replaced by glass block 121 (if required). The color image is transduced by the color image sensor 102 and the resulting image signal is transmitted to the processor/controller 64.

Based on the brightness of the color image, the processor/controller 64 provides a control signal to the multimode light source 52 to adjust the intensity control 80 and thereby adjust the level of light output by the endoscope 60. The processor/controller 64 may also send a control signal to the camera 100 to adjust the gain of the color image sensor 102. After being processed, the color image is displayed on the video monitor 66. All of the imaging operations occur in real-time, that is to say they occur at analog video display rates (30 frames-per-second for NTSC format, and 25 frames-per-second for PAL format).

When switching to the fluorescence/reflectance imaging mode, the processor/controller 64 provides a control signal to the multimode light source 52 to indicate that it should be in fluorescence/reflectance mode. The light source 52 selects and positions the appropriate optical filter 76B into the optical path between the arc lamp 70 and the endoscope light guide 54. This filter 76B transmits those wavelengths of light that will induce the tissue 58 under examination to fluoresce. It also transmits reference reflectance light in either the green or red portions of the visible spectrum or, alternatively, the blue excitation light can be utilized for the reference. All other wavelengths of light are blocked as described below. The filtered light is then projected into the endoscope light guide 54 and is transmitted to the tip of the endoscope 60 to illuminate the tissue 58.

The processor/controller 64 also ensures that the camera 100 is in the correct imaging mode by providing power to the low light image sensor 104. The fluorescence emitted and reference light reflected by the tissue 58, along with the reflected excitation light, are collected by the endoscope image guide 56 and are projected through the camera beam splitter 106 onto the low light image sensor 104 and the color image sensor 102. Spectral filter 118 limits the light transmitted to the low light image sensor 104 to either green or red autofluorescence light only and blocks the light in the excitation and reference wavebands transmitted by light source filter 76B. Spectral filter 119 is inserted into the optical path of the color image sensor 102 during this imaging mode and transmits only the reflected reference waveband light. The reflectance light transmission specifications of filter 119 and light source filter 76B are chosen such that the intensity of the reflected light at the color image sensor 102 results in a transduced image signal with good signal-to-noise characteristics and without significant saturation, while at the same time allowing for excitation of sufficient autofluorescence for imaging. (Note that if spectral filter 119 was located between the beam splitter 106 and the endoscope 60, it would also have to transmit the autofluorescence light detected by the low light image sensor 104.) The autofluorescence image is then transduced by the low light image sensor 104, the reference image is transduced by the color image sensor 102, and the resulting image signals are transmitted to the processor/controller 64.

Based on the brightness of the transduced images, the processor/controller 64 may provide a control signal to the multimode light source 52 to adjust the intensity control 80 and thereby adjust the level of light delivered to the endoscope 60. The processor/controller 64 may also send control signals to the camera 100 to adjust the gains of the low light image sensor 104 and the color image sensor 102 in order to maintain constant image brightness while keeping constant relative gain, as described in more detail below. After being processed, the images from the two sensors are combined into a single image, which is displayed on the video monitor 66. Again, all of the imaging operations occur in real-time.

In order for the combined image to have optimal clinical meaning, for a given proportion of fluorescence to reference light signals emitted by the tissue and received by the system, it is necessary for a consistent proportion to also exist between the processed image signals that are displayed on the video monitor. This implies that the (light) signal response of the fluorescence endoscopy video system is calibrated.

Calibration of the signal response may be implemented in the processor/controller 64. To calibrate the system, the gain response of the fluorescence image sensor and reference image sensor are characterized, and those response characteristics are utilized to establish a constant gain ratio between the fluorescence and reference image signal paths. Of course, when calibrating the light response of a fluorescence endoscopy video system, the entire signal path must be considered. For simplicity, in this embodiment the gains applied to the image signals over the remainder of the image signal path (i.e., excluding the image sensors) are adjusted and are fixed so as not to contribute to the ratio of the overall image signal gains. As a result, maintaining a constant system image signal gain ratio is reduced to establishing a constant gain ratio between the two image sensors.

A method for calibrating the gain response of the fluorescence and reference image sensors will now be described. The particulars of the calibration method depend on the types of sensors utilized. The calibration method described herein is for the preferred sensor types: an ICCD for the low light image sensor 104, and a color CCD for the color image sensor 102.

The gain of an ICCD sensor ($K_{ICCD}$) is typically controlled by varying an analog gain control signal (G). (Such a gain control signal operates on the accelerating voltage that controls the light signal amplification in the intensifier's multichannel plate.) In such sensors, the gain can be varied over about four orders of magnitude of light intensity. The gain/control voltage relationship is approximately exponential and can be characterized by $K_{ICCD} = K_0 \cdot e^{f_{ICCD}(G)}$, where $K_0$ is the overall gain of the ICCD with the gain control setting at zero, and $f_{ICCD}^{(G)} = a_1 \cdot G + a_2 \cdot G^2 + a_3 \cdot G^3$ is a quasilinear function approximated by a polynomial whose coefficients $a_i$ are determined by empirical measurements of the response of the ICCD with varying gain.

The gain of a color CCD can be controlled in two ways: 1) by changing the electronic shutter time (typically in discrete steps) which allows variation in sensitivity over about three orders of magnitude in light intensity, and 2) by changing an analog electronic gain control which allows variation in sensitivity over about one order of magnitude in light intensity. For a CCD, the analog electronic gain typically varies exponentially with a control voltage (R). The gain response of a CCD is thus $K_{CCD} = K_{60} \cdot A_{shutter} \cdot e^{f_{CCD}(R)}$, where $K_{60}$ is the overall CCD gain with the electronic shutter at the standard video field rate (e.g., 1/60 second for NTSC video) and with the control voltage set to zero, $A_{shutter}$ is the attenuation provided by the electronic shutter, and $f_{CCD}(R) = b_{r1} \cdot R + b_{r2} \cdot R^2 + b_{r3} \cdot R^3$ is a quasilinear function approximated by a polynomial whose coefficients $b_i$ are determined by empirical measurements of the CCD response with varying gain. The gain of the CCD can be adjusted to accommodate a wide range in light intensity by varying $A_{shutter}$, which provides step-wise variation over a wide range, in combination with R, which allows continuous variation over a small range.

To maintain a constant relative light signal response from the image sensors, the following gain ratio is maintained constant:

$$\frac{K_{ICCD}}{K_{CCD}} = \frac{K_0 \cdot e^{f_{ICCD}(G)}}{K_{60} \cdot A_{shutter} \cdot e^{f_{CCD}(R)}} = const. \tag{1}$$

This constant gain ratio can be implemented by designating one image sensor as the "master." For a given gain setting of the "master" image sensor, the gain setting of the other image sensor (the "slave") is determined by solving Equation 1 to find the appropriate value of R, $A_{shutter}$ (or G). Either image sensor may be utilized as the master. The choice as to which image sensor is utilized as the master and which the slave depends on factors such as which image signal predominates in the digital domain of the image processor, the technique for solving the equation, and on the time it takes each image sensor to respond to a change in gain.

The gain calibration method required for other types of image sensors utilizes the same principles, including starting with an equation describing the gain of each sensor in terms of controllable parameters, calculating the ratio of the gain equations, assuming the gain ratio is constant, and solving the gain ratio equation for the parameters of one sensor in terms of the parameters of the other sensor and the constant, and can be derived in a similar manner.

In fluorescence/fluorescence mode, the operation of the system is similar to that of fluorescence/reflectance mode, so only the points of difference will be described. Firstly, the light source 52 selects and positions the appropriate optical filter 76C into the optical path between the arc lamp 70 and the endoscope light guide 54. This filter 76C transmits substantially those wavelengths of light that will induce the tissue 58 under examination to fluoresce.

The autofluorescence emitted by the tissue 58 is collected by the endoscope image guide 56 and is projected through the camera beam splitter 106 onto the low light image sensor 104 and the color image sensor 102. Spectral filter 118 limits the light transmitted to the low light image sensor 104 to either green or red autofluorescence light only and excludes light in the excitation waveband. Spectral filter 119 is inserted into the optical path to the color image sensor 102 during this imaging mode and transmits only the autofluorescence light in the waveband not transmitted to the low light image sensor

104. (Note that spectral filter 119 and, if required, glass block 121, cannot be located between the beam splitter 106 and the endoscope 60 for this mode of operation.) The autofluorescence images are then transduced by the low light image sensor 104 and the color image sensor 102 and the resulting image signals are transmitted to the processor/controller 64. After being processed, the images from the two sensors are combined into a single fluorescence/fluorescence image, which is displayed on the video monitor 66. The image sensor gains are controlled in the same calibrated fashion as for fluorescence/reflectance imaging.

Since the autofluorescence image detected with the color image sensor 102 will be very dim, the images obtained with this type of sensor will likely not be acquired, processed and displayed in real-time unless some form of signal amplification (e.g., pixel binning, CCD with charge carrier multiplication, etc.) is provided. Currently, it is also possible to combine a time-averaged image from the color image sensor 102 with a real-time image from the low light image sensor 104 and then display the resulting combined image. Alternatively, images from both sensors could be time-averaged and combined before being displayed.

A second embodiment of this invention will now be described. All points of similarity with the first embodiment will be assumed understood and only points that differ will be described.

Figure 5:
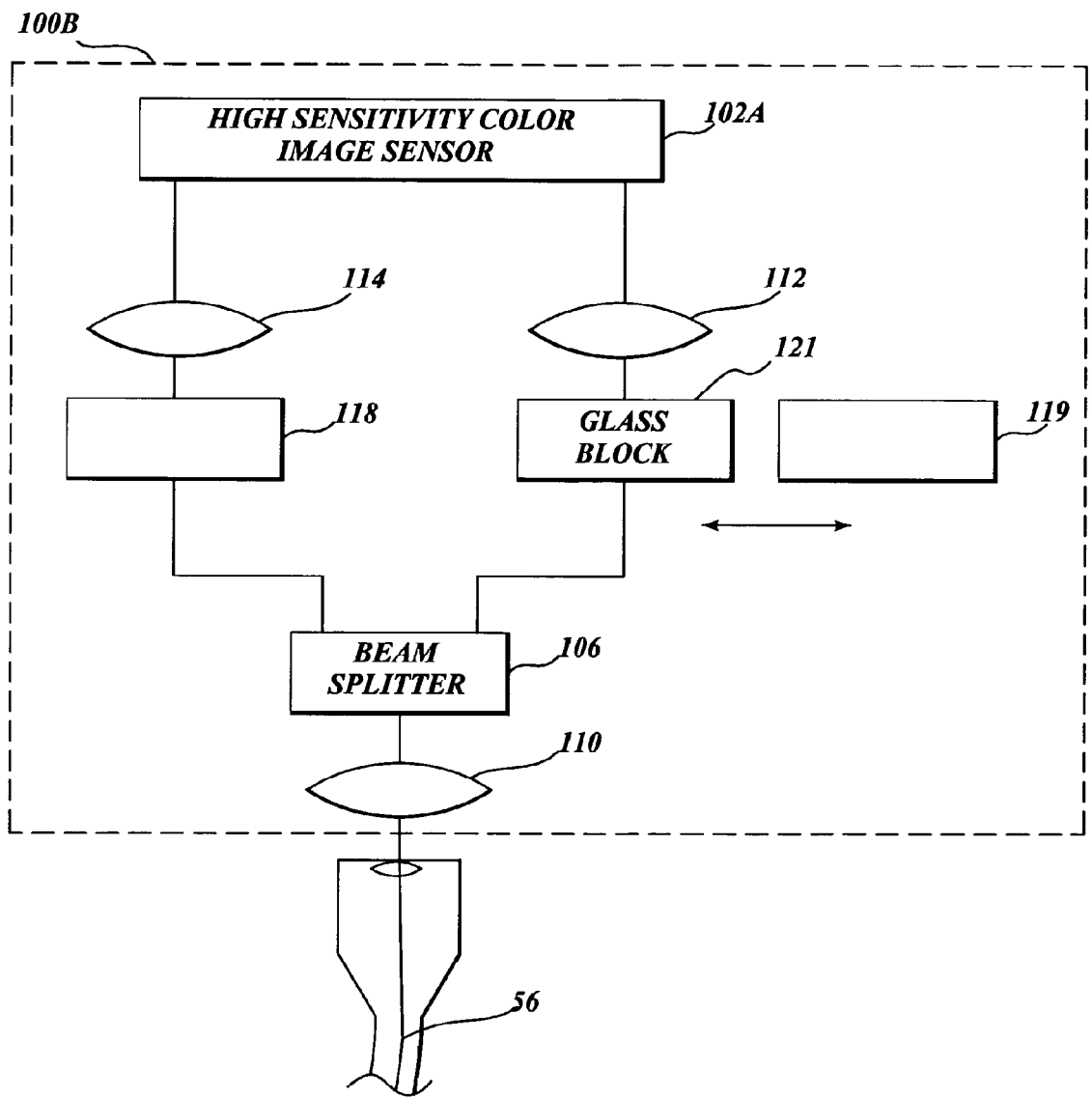
FIG. 5 illustrates a second embodiment of a camera according to the present invention.

In this second embodiment, all aspects of the system are similar to those of the first embodiment except the camera 100A. The camera 100B for this embodiment of a fluorescence endoscopy video system is as shown in FIG. 5. It differs from the camera in the first embodiment in that all imaging modes utilize a single, high sensitivity color image sensor 102A, preferably a CCD with charge carrier multiplication, a three-CCD image sensor assembly with charge carrier multiplication, a color CCD, a three-CCD color image sensor assembly, a color CMOS image sensor, or a three-CMOS color image sensor assembly.

In this embodiment, two images are projected onto the sensor 102A simultaneously. The images are separated and processed by the image processor 64 and displayed according to the imaging mode of the system. In color imaging mode, the color image is separated from the other images, processed and displayed on the video monitor 66. For the color imaging mode, filter 119 is moved out of the light path and glass block 121, if required, is moved into position. For fluorescence/reflectance and fluorescence/fluorescence imaging modes, the fluorescence and reference images are first separated by the image processor 64, processed, and then are again superimposed on the video monitor 66 by applying each image to a different monitor color input.

A direct consequence of using a single high sensitivity color image sensor, as described in this embodiment, is that the gain of the fluorescence and reference images automatically track each other as the gain of the sensor is changed. The gain ratio of the two image signals is determined and maintained by the transmission characteristics of filters 118 and 119 in the camera, and 76B or 76C in the light source. The image processor 64 may also be utilized to implement small changes in the gain ratio by changing the brightness of one image with respect to the other during processing.

As mentioned previously, the autofluorescence images detected with the color image sensor 102A will be very dim, and so the images obtained with this type of sensor will likely not be acquired, processed, and displayed in real-time unless some form of signal amplification (e.g., pixel binning, color CCD with charge carrier multiplication, etc.) is provided. Alternatively, the camera may be used to image autofluorescence in a non-real time mode.

This configuration of the camera also adds an additional restriction to the design of the optical subsystem. The effect of this restriction necessitates that either imaging optical component 112 differs from imaging optical component 114 in such a way that both images are projected onto the same image plane, or that beam splitter 106, after splitting the light from the endoscope 60, utilizes substantially equal optical path lengths for both beams and, in conjunction with similar imaging optical components 112 and 114, projects both images onto the same image plane. Such a beam splitter 106 requires a multicomponent or custom beam splitter 106 of the type shown in FIGS. 4D-E. The beam splitters shown in these drawings also anticipate the need for an equal optical path length, as described for the imaging optics configuration in FIG. 3C.

A third embodiment of this invention will now be described. All points of similarity with the first embodiment will be assumed understood and only points that differ will be described.

Figure 6:
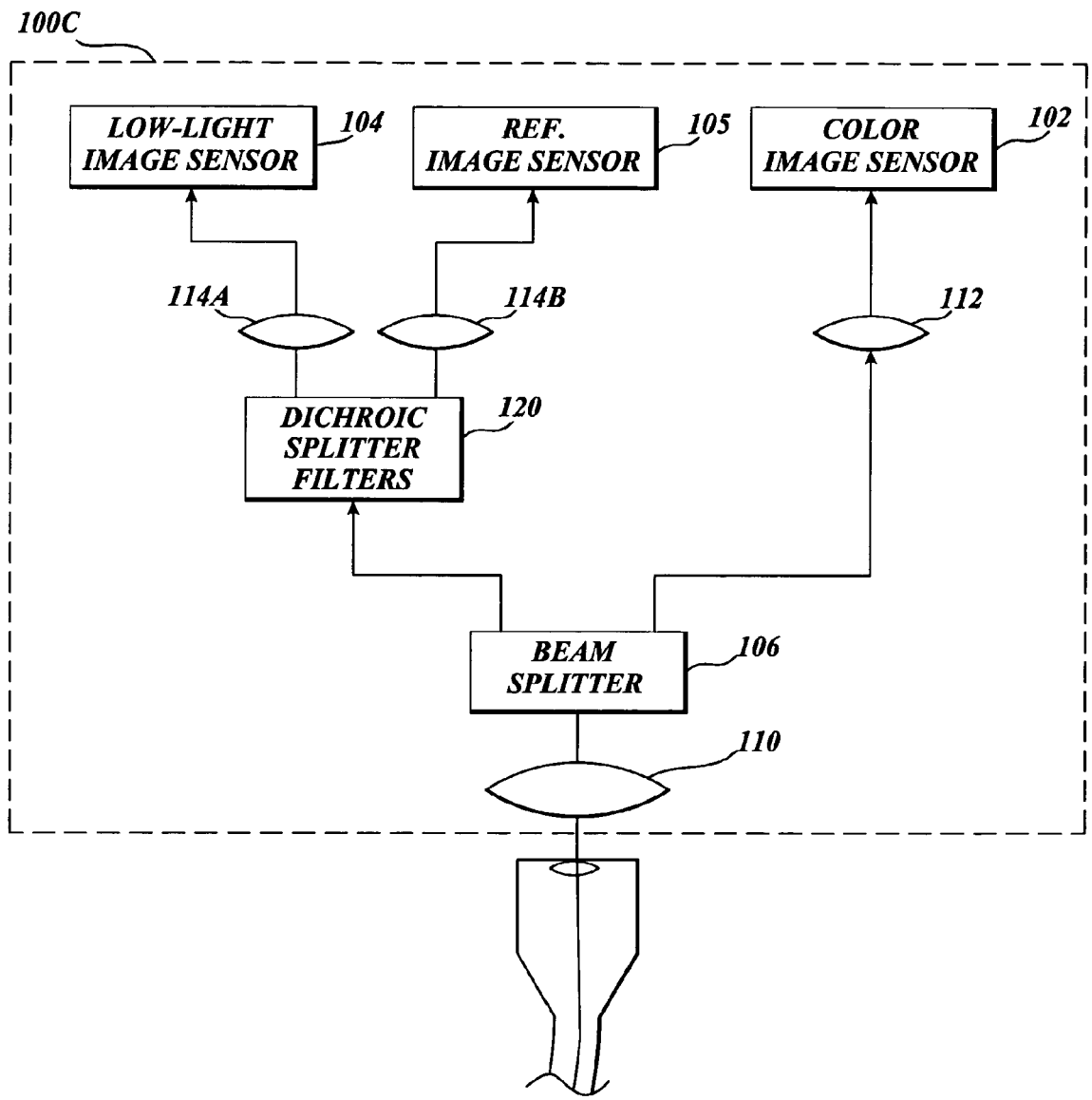
FIG. 6 illustrates a third embodiment of a camera according to the present invention.

In this third embodiment, all aspects of the system are similar to those of the first embodiment except the camera 100A. The camera 100C for this embodiment of a fluorescence endoscopy video system is as shown in FIG. 6. It differs from the camera 100A in the first embodiment in that the color image sensor 102 is utilized only for the color imaging mode. As a consequence, filter 119 has been removed from the color image sensor optical path, which also eliminates the need for a filter moving mechanism. Instead, the light that is not being projected towards the color image sensor 102 after being split by the beam splitter 106 is projected towards a dichroic splitting and filtering assembly 120. This assembly 120 further splits and filters the light from the beam splitter 106 into two spectral components.

Rather than splitting the incoming light into two beams with the same spectrum but a fractional intensity of the incoming light, a dichroic splitter 120 divides the incoming light spectrally, so that certain wavelengths are reflected while others are transmitted. Further filtering may then be applied to this spectrally divided light beam.

Several possible configurations for such a dichroic splitting and filtering assembly 120 are shown in FIG. 7. As shown in the figure, the dichroic splitting and filtering assembly 120 may comprise a cube dichroic 130 or a plate dichroic 133. Spectral filters 118, 119 may be positioned away from the dichroic mirrors or, in the case of the cube, may be formed as a coating on the cube. In addition, with either embodiment, a reflecting mirror 140 may be used to invert the image reflected off the dichroic mirror. In addition, the dichroic splitter may be configured as a custom prism assembly as shown in FIG. 9.

It should again be noted that if the optical path between the endoscope 60 and image sensors contains an uneven number of reflections (e.g., such as from a single component beam splitter or dichroic), the image projected onto the sensor will be left-to-right inverted. The orientation of such images will need to be corrected by image processing.

After exiting the assembly 120, one of the spectral components is projected onto the low light image sensor 104 and the second component is projected onto a separate reference sensor 105. The reference sensor 105 preferably comprises a monochrome CCD, monochrome CCD with charge carrier multiplication, ICCD, CID, CMD, CMOS or EBCCD-type sensor, but it may also be a color CCD, a three-CCD color image sensor assembly, a color CCD with charge carrier multiplication, a three-color CCD image sensor assembly with charge carrier multiplication, a color CMOS image sensor, or a three-CMOS color image sensor assembly. In the case of a color image sensor, depending on the sensitivity of the sensor, autofluorescence images obtained will likely not be acquired, processed and displayed in real-time unless some form of signal amplification (e.g., pixel binning, CCD with charge carrier multiplication, etc.) is provided. Alternatively, for fluorescence/fluorescence mode operation, the camera may combine a real-time autofluorescence image (from the low light image sensor 104) with a time-averaged image from the referenced sensor 105, or may provide all autofluorescence images in non-real time mode.

Calibration of the light signal path for this embodiment is similar to that of the first embodiment for the preferred choice of image sensors, in which an ICCD is the low light image sensor 104 and a CCD is the reference image sensor 105. For the case in which the reference image sensor is also an intensified sensor such as an ICCD or EBCCD, the equation describing the gain ratio for the two sensors is slightly different.

As mentioned above, the gain/control voltage characteristics of an ICCD (or EBCCD) image sensor is approximately exponential and can be characterized by $K_{ICCD}=K_0 \cdot e^{f_{CCD}(G)}$, where $K_0$ is the overall gain of the ICCD with the gain control setting at zero, G is the intensifier gain signal, and $f_{ICCD}^{(G)}=a_1 \cdot G + a_2 \cdot G^2 + a_3 \cdot G^3$ is a quasilinear function approximated by a polynomial whose coefficients $a_i$ are determined by empirical measurements of the response of the ICCD with varying gain.

With two ICCDs, the gain ratio to be maintained constant is $$\frac{K_{ICCD_{fluor}}}{K_{ICCD_{ref}}} = \frac{K_{0_{fluor}} \cdot e^{f_{ICCDfluor}(G_{fluor})}}{K_{0_{ref}} \cdot e^{f_{ICCD_{ref}}(G_{ref})}} = const. \quad (2)$$

As described in previous embodiments, the gain setting $G_{fluor}$ (or $G_{ref}$) of one image sensor (the "master") is determined by an automatic gain control. The gain setting of the other image sensor (the "slave") is determined by solving Equation 2 to find the appropriate value of $G_{ref}$ (or $G_{fluor}$). As discussed previously, either image sensor may be utilized as the master.

A fourth embodiment of this invention will now be described. All points of similarity with the third embodiment will be assumed understood and only points that differ will be described.

Figure 8:
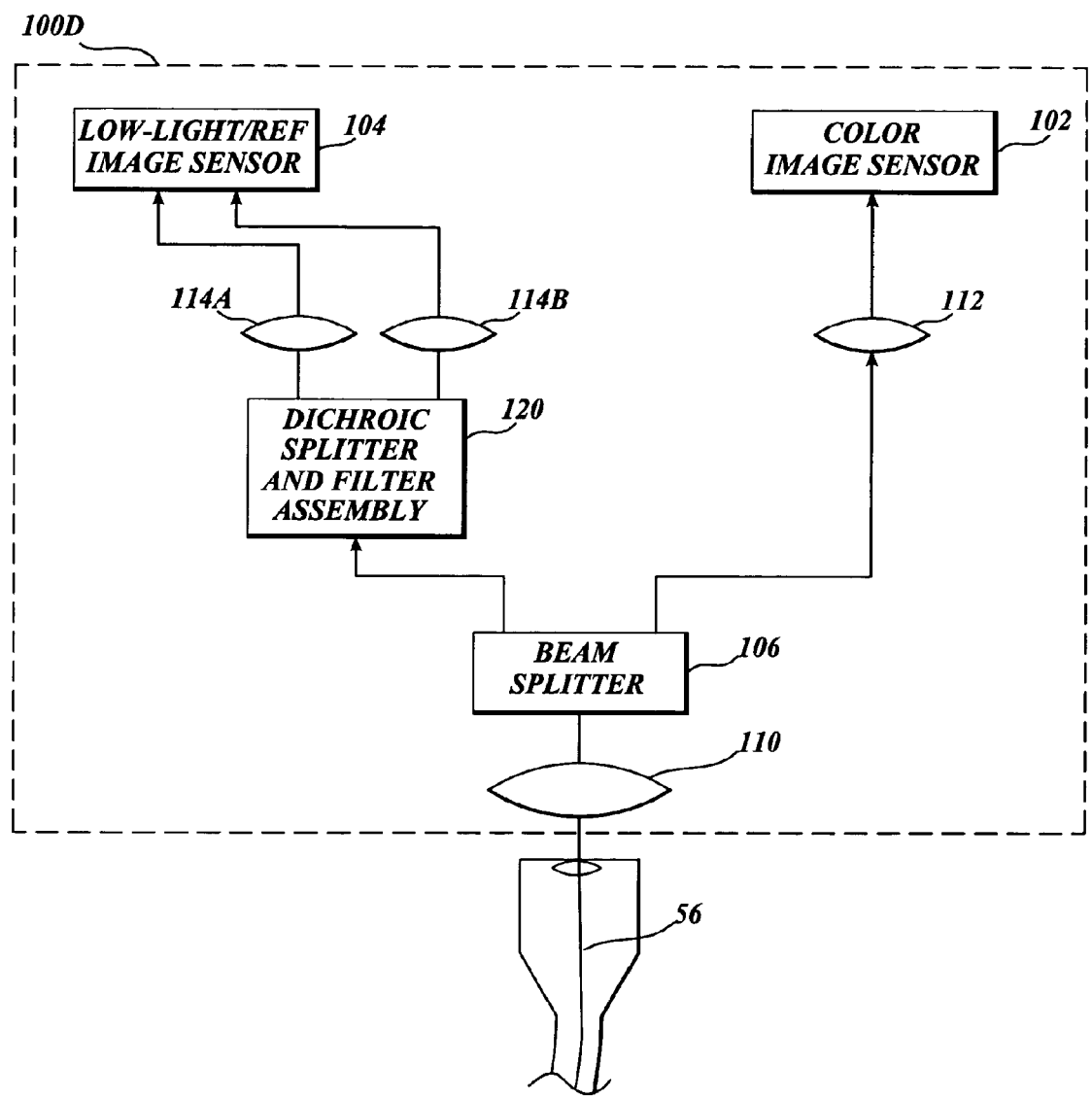
FIG. 8 illustrates a fourth embodiment of a camera according to the present invention.

In this fourth embodiment, all aspects of the system are similar to those of the third embodiment except the camera 100C The camera 100D for this embodiment of a fluorescence endoscopy video system is as shown in FIG. 8. It differs from the camera 100C in the third embodiment in that the low light image sensor 104 is utilized to image both the first fluorescence image as well as the reference fluorescence or reflectance image.

As with the configuration of the beam splitter 106 in the second embodiment, the configurations of the dichroic splitter and filter assembly 120 and, if necessary, in combination with imaging optical components 114A and 114B, project both the primary fluorescence and the reference image into the same image plane.

Figure 9A:
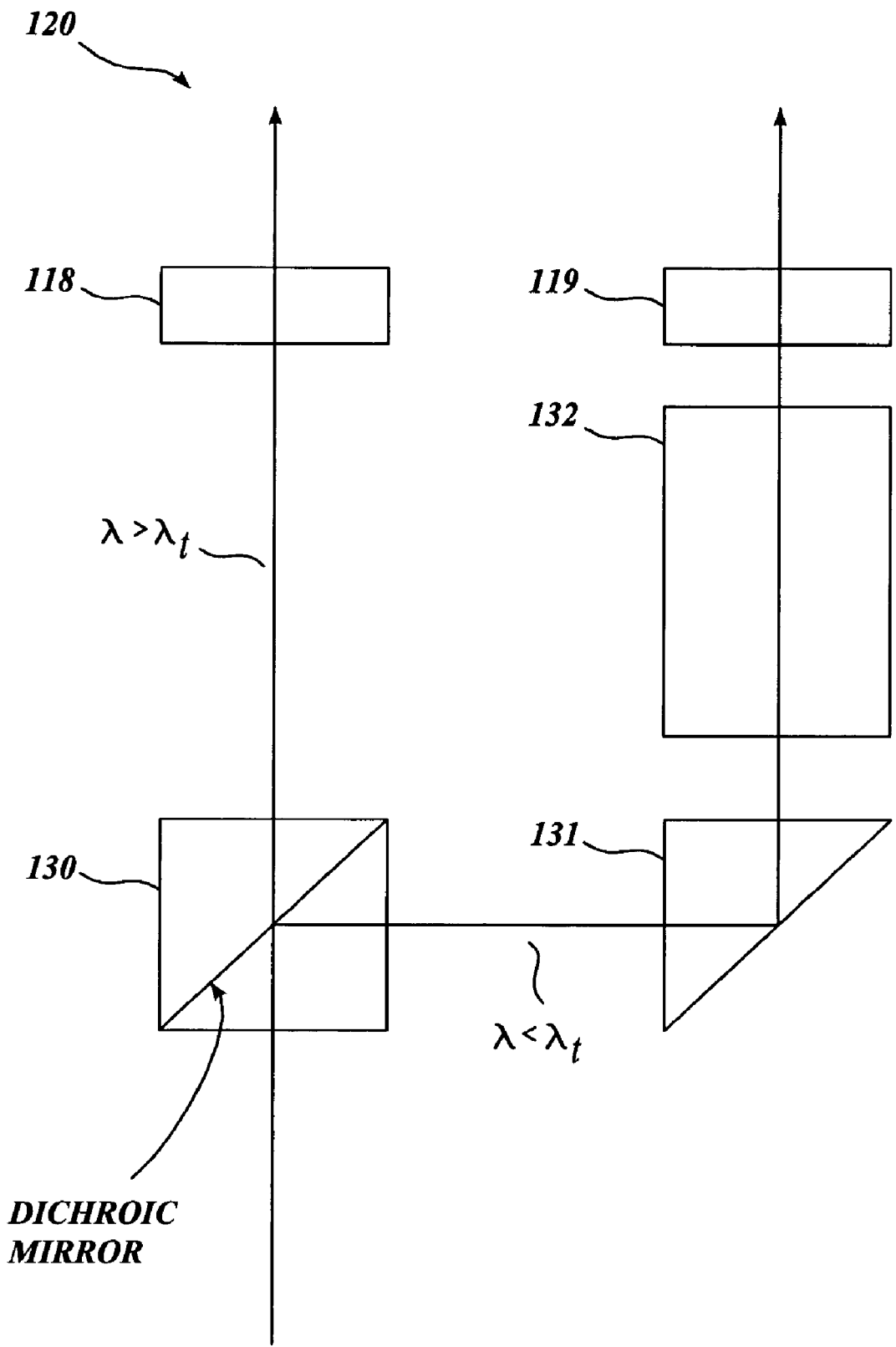
FIG. 9 illustrates examples of spectral splitter and filtering assembly that can transmit images to the same image plane.
Figure 9B:
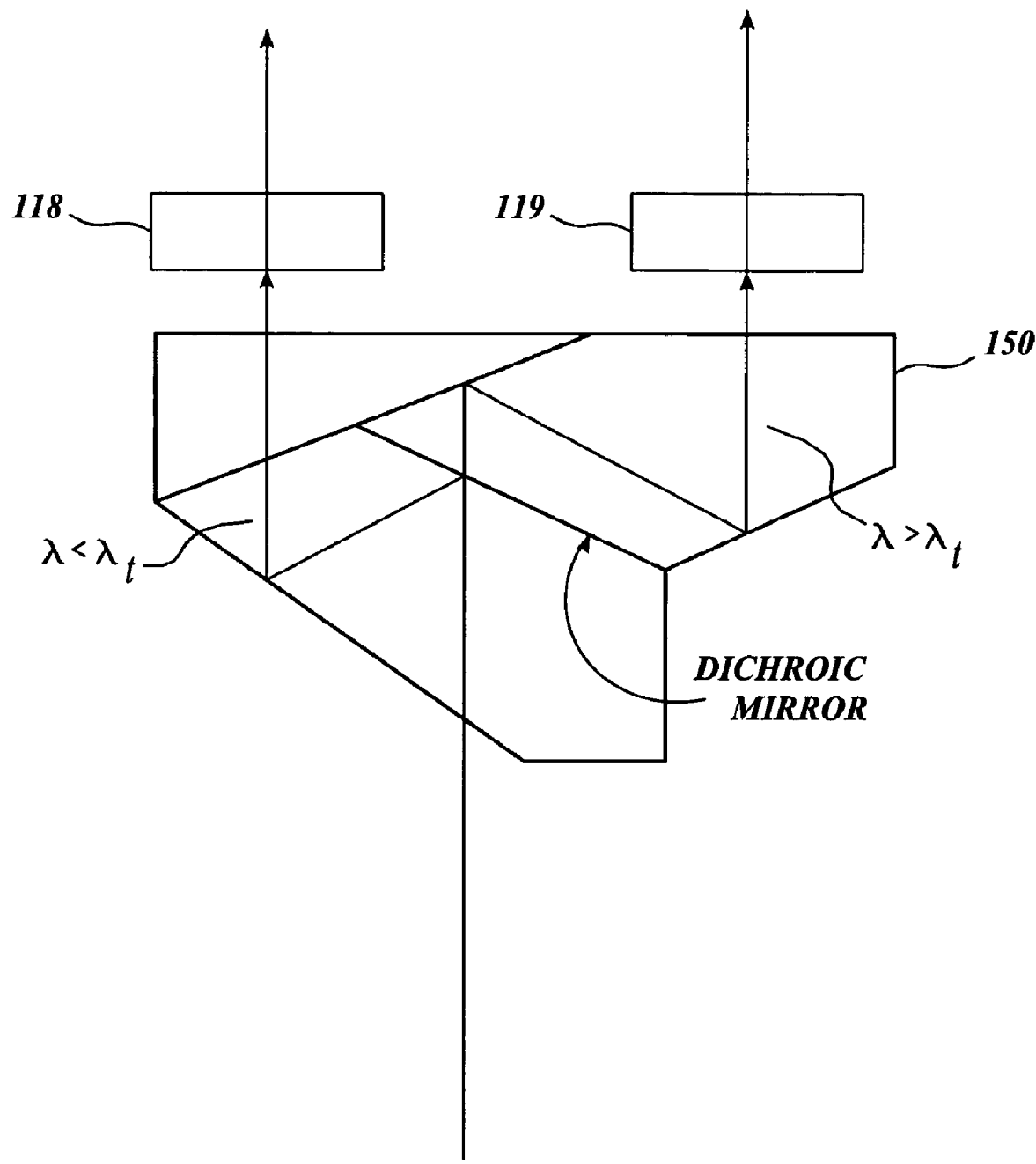

To project the light that passes through the dichroic mirror and the light that is reflected off the dichroic mirror in the same plane, the dichroic assembly 120 may include a right angle prism 131 and a glass block 132 that compensate for the differing optical path lengths as shown in FIG. 9A. Alternatively, as shown in FIG. 9B, the dichroic assembly 120 may include a number of prisms having partially and fully reflective surfaces in the same configured manner as the beam splitter shown in FIG. 4E, except that the partially reflecting surface 95 is replaced with a dichroic mirror surface. In another alternative, the imaging optical component 114A differs from imaging optical component 114B in such a way that both images are projected onto the same image plane.

When using the camera shown in FIG. 8 for fluorescence/reflectance imaging, the transmission of the filter used for the reference reflectance image (e.g., 114B) and light source filter 76B in FIG. 2 is chosen in such a way that the intensity of the reference reflected image at sensor 104 is similar to that of the fluorescence image for all possible excitation light intensities. Also in similar fashion to that described for the second embodiment, the images transduced by the low light image sensor 104 are separated by the image processor 64, are processed, and then are again superimposed on the video monitor 66 by applying each image to a different monitor color input. A fluorescence endoscopy video system utilizing this embodiment is calibrated in a similar manner to that described in the second embodiment to maintain constant gain ratio.

A fifth embodiment of this invention will now be described. All points of similarity with the first embodiment will be assumed understood and only points that differ will be described.

Figure 10:
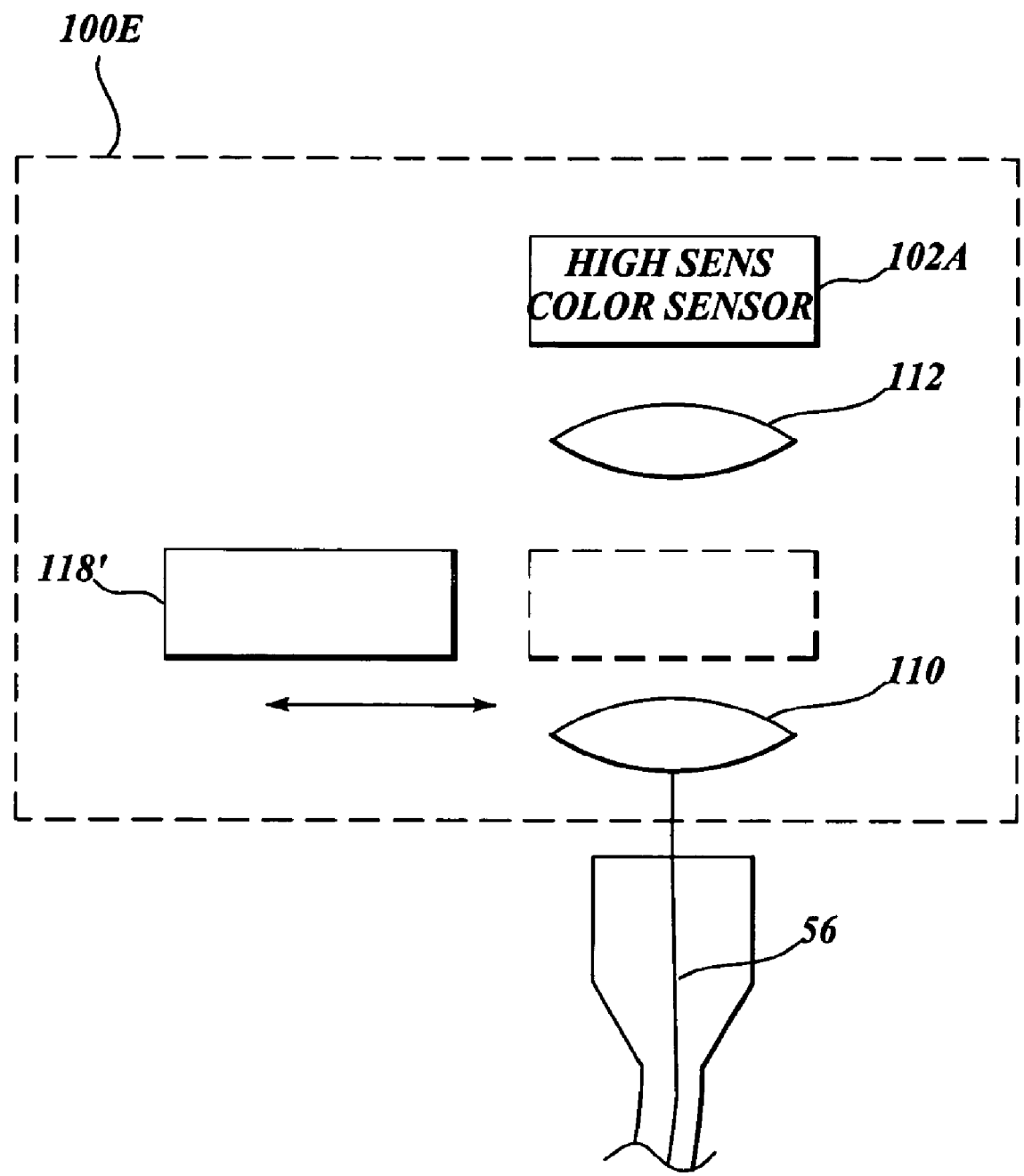
FIG. 10 illustrates a fifth embodiment of a camera according to the present invention.

In this fifth embodiment, all aspects of the system are similar to those of the first embodiment except the camera 100A. The camera 100E for this embodiment of a fluorescence endoscopy video system is as shown in FIG. 10. It differs from the camera 100A in the first embodiment in that all imaging modes utilize a single, high sensitivity color image sensor 102A. It differs from the camera in the second embodiment in that the beam splitter is removed and the need for spectral filters 118 and 119 is eliminated. Each of the pixel elements on the high sensitivity color sensor 102A is covered by an integrated filter, typically red, green, or blue. These filters block the reflected excitation light and allow the fluorescence and reflectance light to reach the pixel elements. Alternatively, if it is not possible to achieve sufficient blocking of the excitation light by means of filters on the color image sensor, a separate blue blocking filter 118' can be provided. The blue blocking filter 118' is a long pass filter that blocks light at blue and shorter wavelengths and transmits light at green and longer wavelengths. When such a blue blocking filter 118' is utilized, the intensity of the reflected excitation light is reduced to the point that the integrated filters on the pixel elements provide sufficient further filtering to define the wavelengths of fluorescence and reflectance light that reach the high sensitivity color sensor 102A.

In this embodiment, the primary fluorescence and reference images are superimposed over the same area of the image sensor 102A but, because of the individual filters placed over each pixel, these images are detected by different sensor pixels. Separate primary fluorescence and reference image signals can then be created by the image processor 64 from the single CCD image signal.

In the color imaging mode, if it is utilized for fluorescence imaging, the blue blocking filter 118' is removed from the light path and, if required, glass block 121 is moved into position. The color image is processed by image processor 64 and displayed on the video monitor 66. For fluorescence/reflectance and fluorescence/fluorescence imaging modes the fluorescence and reference images are processed by image processor 64 and superimposed on the video monitor 66 by applying each image to a different color input of the monitor.

The way in which this embodiment is calibrated to maintain constant relative gain is similar to that described for the second embodiment.

The reference light transmission specifications of both the light source filter 76B or 76C and the selective color filters integrated with the image sensor 102A are chosen such that the intensity of the reflected light at the color image sensor active elements results in a transduced image signal with good signal-to-noise characteristics and without significant saturation. At the same time these filters must have appropriate light transmission specifications for excitation and imaging of the primary fluorescence. The filter transmission characteristics must further be chosen to provide the desired ratio of relative primary fluorescence to reference light intensity at the image sensor.

As mentioned previously, the autofluorescence images detected with the color image sensor will be very dim, and so the images obtained with this type of sensor will likely not be acquired, processed and displayed in real-time unless some form of signal amplification (e.g., pixel binning, CCD with charge carrier multiplication, etc.) is provided. Alternatively, the camera may be used to image autofluorescence in non-real time mode.

As will be appreciated, each of the embodiments of the camera described above are lighter in weight than prior art because no more than one low light image sensor 104 is required. Since such sensors are often heavy, bulky and expensive, the size and cost of the camera is significantly reduced. Furthermore, because a fixed beam splitter 106 is used instead of a movable mirror, the cameras are more robust and can be made less expensively.

As indicated above, the filters in the light source and camera should be optimized for the imaging mode of the camera, the type of tissue to be examined, and/or the type of pre-cancerous tissue to be detected. Although all of the filters described below can be obtained made to order using standard, commercially available components, the appropriate wavelength range of transmission and degree of blocking outside of the desired transmission range for the described fluorescence endoscopy images modes are important to the proper operation of the system. The importance of other issues in the specification of such filters such as the fluorescence properties of the filter materials and the proper use of anti-reflection coatings are taken to be understood.

FIGS. 11-14 illustrate the preferred filter characteristics for use in a fluorescence endoscopy video system operating in fluorescence/reflectance imaging mode wherein both tissue autofluorescence is being excited and imaged and a reference reflectance light is being reflected and imaged. There are several possible configurations of fluorescence endoscopy video systems, operating in the fluorescence/reflectance imaging mode including green fluorescence with either red or blue reflectance, and red fluorescence with either green, blue, or near-infrared reflectance. The particular configuration utilized depends on the target clinical organ and application. The filter characteristics will now be described for each of these four configurations.

Figure 11A:
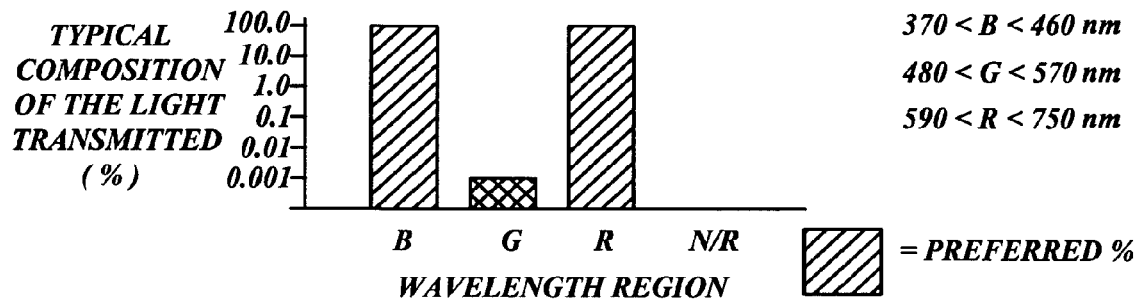
FIGS. 11A-11D are graphs illustrating presently preferred transmission characteristics of filters and dichroic splitters for fluorescence/reflectance imaging using green fluorescence light and red reflectance light.

FIGS. 11A-11D illustrate the preferred composition of the light transmitted by filters for a green fluorescence and red reflectance imaging mode. FIG. 11A illustrates the composition of the light transmitted by the light source filter, such as filter 76B, which is used to produce blue excitation light and red reference light. This filter transmits light in the blue wavelength range from 370-460 nm, or any subset of wavelengths in this range. It also transmits light in the red wavelength range of 590-750 nm, or any subset of wavelengths in this range. The light transmitted in the red wavelength range (or subset of that range) is adjusted, as part of the system design, to be an appropriate fraction of the light transmitted in the blue wavelength range. This fraction is selected to meet the need to match the intensity of the reflected reference light projected on the color image sensor to the requirements of the sensor, at the same time as maintaining sufficient fluorescence excitation. Of the light transmitted by this filter, less than 0.001% is in the green wavelength range of 480-570 nm (or whatever desired subset of this range is specified as the transmission range of the green fluorescence filter described below).

Figure 11B:
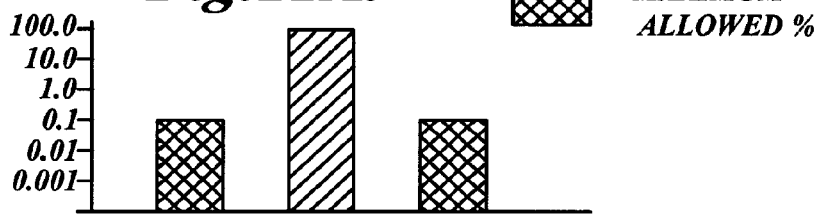

FIG. 11B shows the composition of the light transmitted by a camera filter, such as spectral filter 118, for imaging the green fluorescence image. In this configuration, the filter blocks the blue excitation light and red reflectance light while transmitting green fluorescence light in the wavelength range of 480-570 nm, or any subset of wavelengths in this range. When used in a fluorescence endoscopy video system with the light source filter 76B described above and the dichroic mirror described below, the filter characteristics are such that any light outside of the wavelength range of 480-570 nm (or any desired subset of wavelengths in this range) contributes no more than 0.1% to the light transmitted by the filter.

Figure 11C:
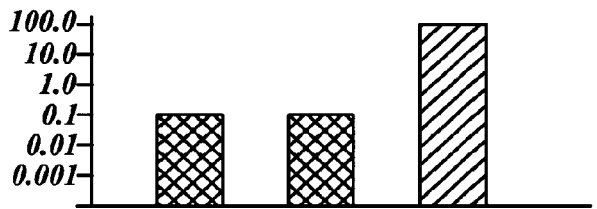

FIG. 11C shows the composition of the light transmitted by a camera filter, such as spectral filter 119, for imaging the red reflectance image. In this configuration, the filter blocks the blue excitation light and green fluorescence light while transmitting red reflectance light in the wavelength range of 590-750 nm, or any desired subset of wavelengths in this range. When used in a fluorescence endoscopy video system with the light source filter 76B described above and the dichroic mirror described below, the filter characteristics are such that any light outside of the wavelength range of 590-750 nm (or any desired subset of wavelengths in this range) contributes no more than 0.1% to the light transmitted by the filter. If the reference image sensor is a color image sensor, such as a color CCD, then further filtering may be obtained from the color filters integrated with the sensor. The in-band transmission characteristics (in the wavelength range of 590-750 nm, or any desired subset of wavelengths in this range) are determined by the need to match the intensity of the reflected reference light projected onto the color image sensor to the requirements of the sensor, in combination with the characteristics of the light source filter described above.

Figure 11D:
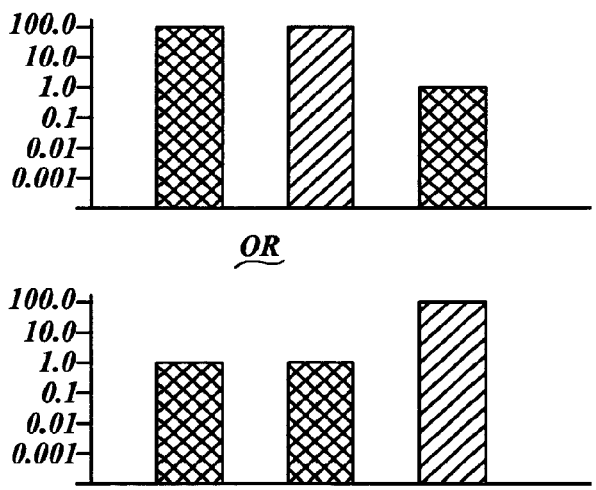

FIG. 11D shows the composition of the light transmitted by a dichroic mirror of the kind that may be employed in the dichroic splitter and filter assembly 120. The dichroic mirror preferably has a half-maximum transmission in the range of 570-590 nm. It may reflect the shorter wavelengths and transmit the longer wavelengths (long pass) or transmit shorter wavelengths and reflect longer wavelengths (short pass). As described above, the dichroic splitter and filter assembly may incorporate the filters shown in FIGS. 11B and 11C.

Figure 12A:
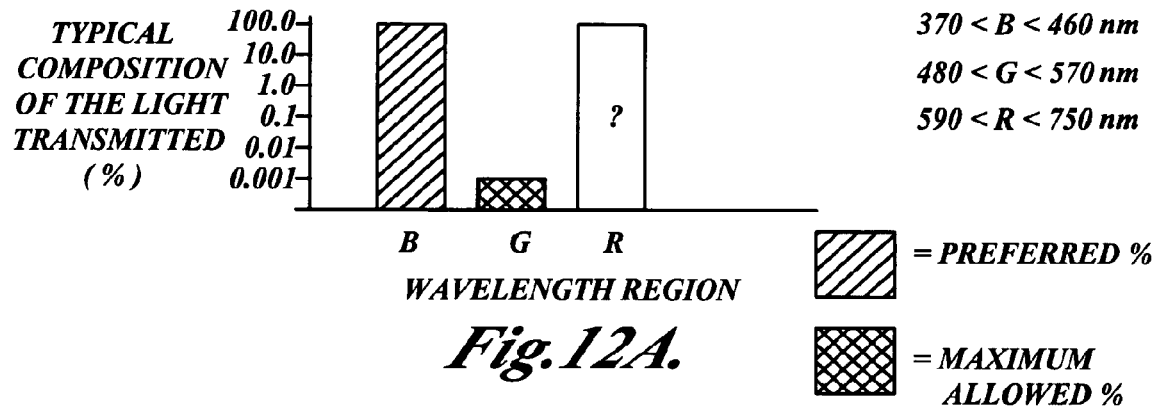
FIGS. 12A-12D are graphs illustrating presently preferred transmission characteristics for filters and dichroic splitters for fluorescence/reflectance imaging using green fluorescence light and blue reflectance light.

FIGS. 12A-12D illustrate the preferred composition of the light transmitted by filters for a green fluorescence and blue reflectance imaging mode. FIG. 12A illustrates the composition of the light transmitted by a light source filter which is used to produce excitation light, such as filter 76B described above. In the case of a fluorescence/reflectance imaging mode utilizing blue reflectance, the wavelengths of the imaged reflectance light are contained within the range of blue excitation wavelengths. The filter transmits light in the wavelength range from 370-460 nm, or any subset of wavelengths in this range, but it is not required to transmit any light in the red wavelength range. Of the light transmitted by this filter, less than 0.001% is in the green wavelength range of 480-570 nm (or whatever desired subset of this range is specified as the transmission range of the green fluorescence filter described below).

Figure 12B:
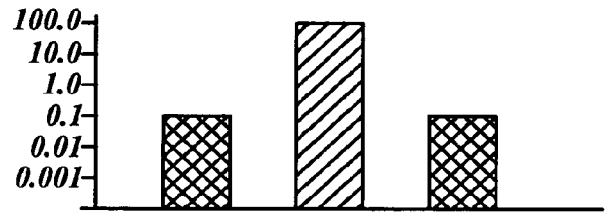

FIG. 12B shows the composition of the light transmitted by a camera filter for imaging the green fluorescence image, such as spectral filter 118. The composition of the light transmitted by this filter has the same characteristics as the light described in FIG. 11B.

Figure 12C:
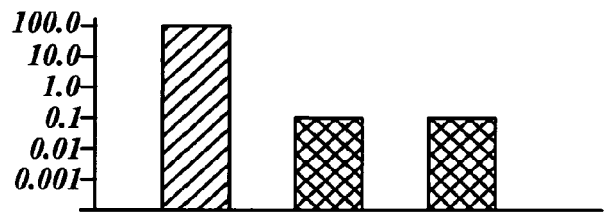

FIG. 12C shows the composition of the light transmitted by a camera filter, such as filter 119, for imaging the blue reflectance image. In this configuration, the filter blocks the green fluorescence light while transmitting blue reflectance light in the wavelength range of 370-460 nm, or any desired subset of wavelengths in this range. Depending on the sensitivity of the image sensor used to transduce the blue reflectance image, the transmission of this filter may need to be restricted so as to prevent the large amount of reflected blue light from overwhelming the sensor. When used in a fluorescence endoscopy video system with the light source filter 76B described above and the dichroic mirror described below, the filter characteristics are such that any light outside of the wavelength range of 370-460 nm, or any desired subset of wavelengths in this range, contributes no more than 0.1% to the light transmitted by the filter. If the reference image sensor is a color image sensor, such as a color CCD, then further filtering of the reflected blue light may be obtained from the color filters integrated with the sensor.

Figure 12D:
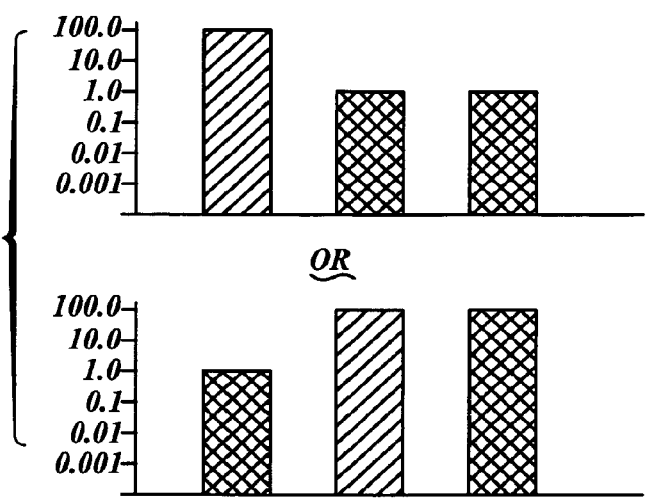

FIG. 12D shows the composition of the light transmitted by a dichroic mirror of the kind that may be employed in the dichroic splitter and filter assembly 120. The dichroic mirror preferably has a half-maximum transmission in the range of 460-480 nm. It may reflect the shorter wavelengths and transmit the longer wavelengths (long pass) or transmit shorter wavelengths and reflect longer wavelengths (short pass). As described above the dichroic splitter and filter assembly may incorporate the filters shown in FIGS. 12B and 12C.

Figure 13A:
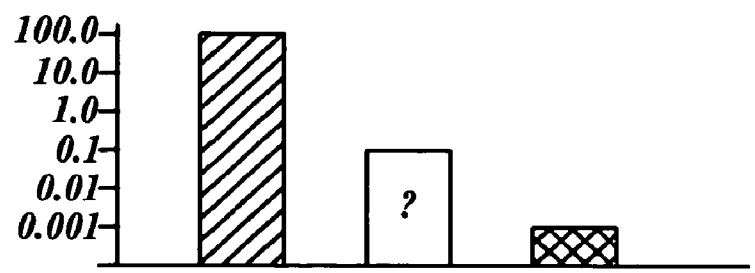
FIGS. 13A-13D are graphs illustrating presently preferred transmission characteristics of filters and dichroic splitters for fluorescence/reflectance imaging using red fluorescence light and blue reflectance light.

FIGS. 13A-13D illustrate the preferred composition of the light transmitted by filters for a red fluorescence and blue reflectance imaging mode. FIG. 13A illustrates the composition of the light transmitted by a light source filter, such as filter 76B, which is used to produce blue excitation light. This filter transmits light in the wavelength range from 370-460 nm, or any subset of wavelengths in this range. Of the light transmitted by this filter, less than 0.001% is in the red fluorescence imaging wavelength range of 590-750 nm (or whatever desired subset of this range is specified as the transmission range of the red fluorescence filter described below).

Figure 13B:
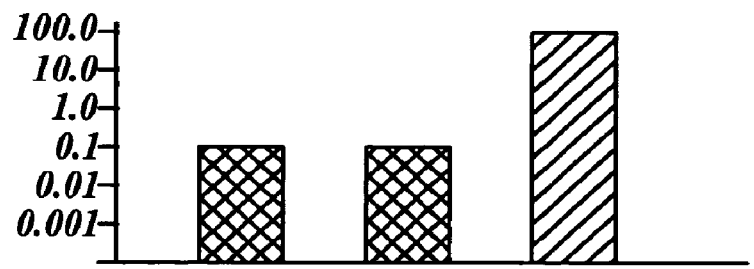

FIG. 13B shows the composition of the light transmitted by a camera filter, such as spectral filter 118, for imaging the red fluorescence image. In this configuration, the filter blocks the blue excitation light, while transmitting red fluorescence light in the wavelength range of 590-750 nm, or any subset of wavelengths in this range. When used in a fluorescence endoscopy video system with the light source filter 76B described above and the dichroic mirror described below, the filter characteristics are such that any light outside of the wavelength range of 590-750 nm, or any desired subset of wavelengths in this range, contributes no more than 0.1% to the light transmitted by the filter.

Figure 13C:
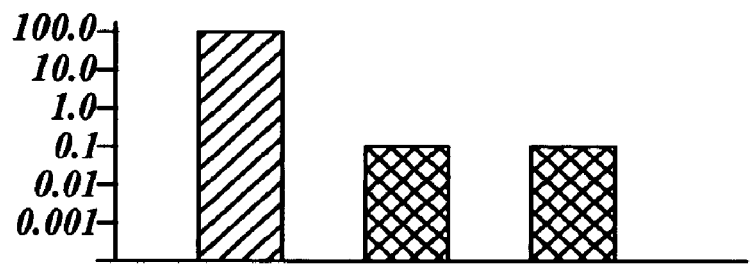

FIG. 13C shows the composition of the light transmitted by a camera filter, such as filter 119, for imaging the blue reflectance image. The composition of the light transmitted by this filter has the same characteristics as the light described in FIG. 12C.

Figure 13D:
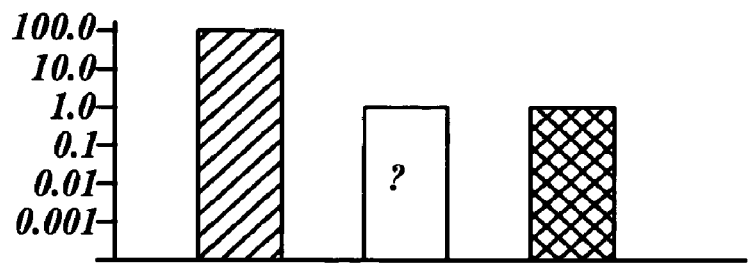

FIG. 13D shows the composition of the light transmitted by a dichroic mirror of the kind that may be employed in the dichroic splitter and filter assembly 120 to split the red fluorescence and blue reflectance. The dichroic mirror preferably has a half-maximum transmission in the range of 460-590 nm. It may reflect the shorter wavelengths and transmit the longer wavelengths (long pass) or transmit shorter wavelengths and reflect longer wavelengths (short pass). As described above the dichroic splitter and filter assembly may incorporate the filters described in FIGS. 13B and 13C.

Figure 14A:
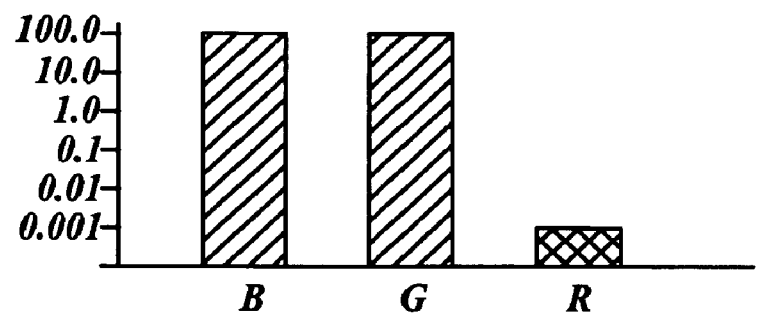
FIGS. 14A-14D are graphs illustrating presently preferred transmission characteristics of filters and dichroic splitters for fluorescence/reflectance imaging using red fluorescence light and blue reflectance light.

FIGS. 14A-14D illustrate the preferred composition of the light transmitted by filters for a red fluorescence and green reflectance imaging mode. FIG. 14A illustrates the composition of the light transmitted by a light source filter which is used to produce excitation light, such as filter 76B described above. This filter transmits light in the blue wavelength range from 370-460 nm, or any subset of wavelengths in this range. It also transmits light in the green wavelength range of 480-570 nm, or any subset of wavelengths in this range. The light transmitted in the green wavelength range (or subset of that range) is adjusted, as part of the system design, to be an appropriate fraction of the light transmitted in the blue wavelength range. This fraction is selected to meet the need to match the intensity of the reflected reference light projected on the color image sensor to the requirements of the sensor, at the same time as maintaining sufficient fluorescence excitation. Of the light transmitted by this filter, less than 0.001% is in the red fluorescence imaging wavelength range of 590-750 nm (or whatever desired subset of this range is specified as the transmission range of the red fluorescence filter described below).

Figure 14B:
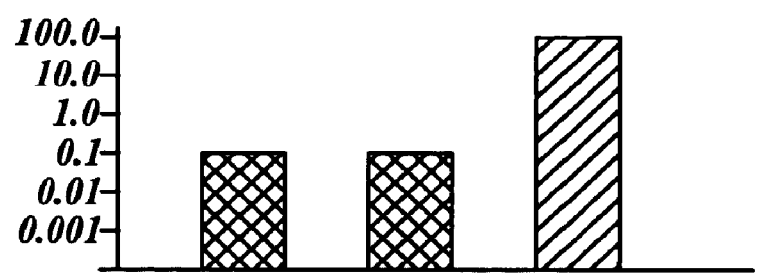

FIG. 14B shows the composition of the light transmitted by a camera filter, such as spectral filter 118, for imaging the red fluorescence image. In this configuration, the filter blocks the blue excitation light and green reflectance light while transmitting red fluorescence light in the wavelength range of 590-750 nm, or any subset of wavelengths in this range. When used in a fluorescence endoscopy video system with the light source filter 76B described above and the dichroic mirror described below, the filter characteristics are such that any light outside of the wavelength range of 590-750 nm, or any desired subset of wavelengths in this range, contributes no more than 0.1% to the light transmitted by the filter.

Figure 14C:
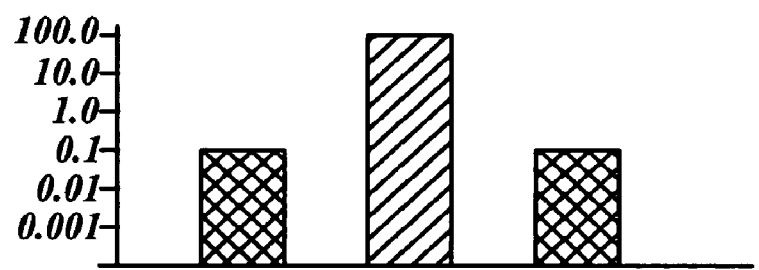

FIG. 14C shows the composition of the light transmitted by a camera filter, such as filter 119, for imaging the green reflectance image. In this configuration, the filter blocks the blue excitation light and red fluorescence light while transmitting green reflectance light in the wavelength range of 480-570 nm, or any desired subset of wavelengths in this range. The in-band transmission characteristics (in the wavelength range of 480-570 nm, or any desired subset of wavelengths in this range) are determined by the need to match the intensity of the reflected reference light projected onto the color image sensor to the requirements of the sensor, in combination with the characteristics of the light source filter described above. When used in a fluorescence endoscopy video system with the light source filter 76B described above and the dichroic mirror described below, the filter characteristics are such that any light outside of the wavelength range of 480-570 nm, or any desired subset of wavelengths in this range, contributes no more than 0.1% to the light transmitted by the filter.

Figure 14D:
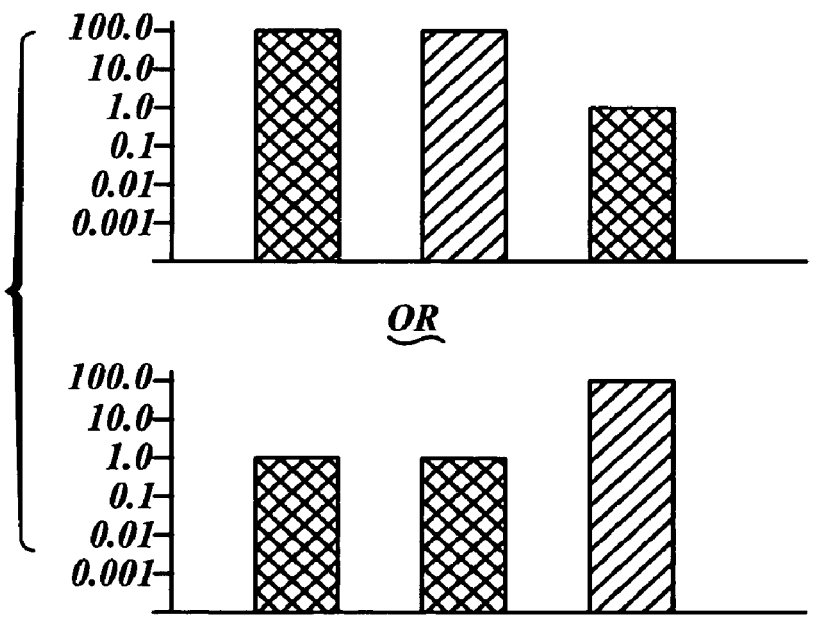

FIG. 14D shows the composition of the light transmitted by a dichroic mirror of the kind that may be employed in the dichroic splitter and filter assembly 120 to split the red fluorescence and green reflectance. The composition of the light transmitted by this filter has the same characteristics as the light described in FIG. 11D.

Figure 15A:
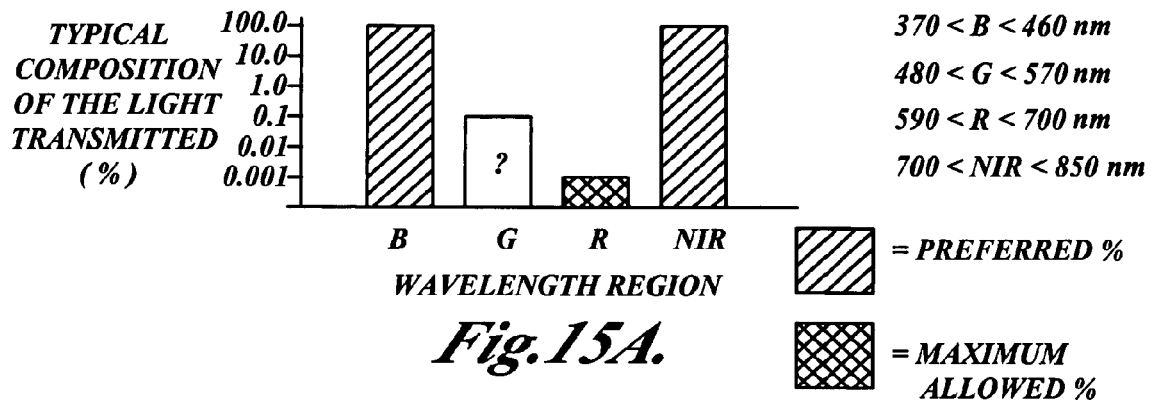
FIGS. 15A-15D are graphs illustrating presently preferred transmission characteristics of filters and dichroic splitters for fluorescence/reflectance imaging using red fluorescence light and near-infrared reflectance light.

FIGS. 15A-15D illustrate the preferred composition of the light transmitted by filters for a red fluorescence and near-infrared reflectance imaging mode. FIG. 15A illustrates the composition of the light transmitted by a light source filter, which is used to produce excitation light such as filter 76B described above. This filter transmits light in the blue wavelength range from 370-460 nm, or any subset of wavelengths in this range. It also transmits light in the near-infrared wavelength range of 700-850 nm, or any subset of wavelengths in this range. The light transmitted in the near-infrared wavelength range (or subset of that range) is adjusted, as part of the system design, to be an appropriate fraction of the light transmitted in the blue wavelength range to meet the need to match the intensity of the reflected reference light projected on the color image sensor to the requirements of the sensor, at the same time as maintaining sufficient fluorescence excitation. Of the light transmitted by this filter, less than 0.001% is in the red fluorescence imaging wavelength range of 590-700 nm (or whatever desired subset of this range is specified as the transmission range of the red fluorescence filter described below).

Figure 15B:
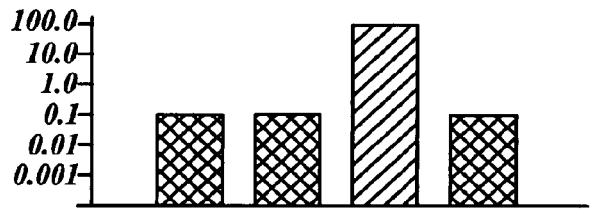

FIG. 15B shows the composition of the light transmitted by a camera filter, such as spectral filter 118, for imaging the red fluorescence image. In this configuration, the filter blocks the blue excitation light and near-infrared reflectance light while transmitting red fluorescence light in the wavelength range of 590-700 nm, or any subset of wavelengths in this range. When used in a fluorescence endoscopy video system with the light source filter 76B described above and the dichroic mirror described below, the filter characteristics are such that any light outside of the wavelength range of 590-700 mm, or any desired subset of wavelengths in this range, contributes no more than 0.1% to the light transmitted by the filter.

Figure 15C:
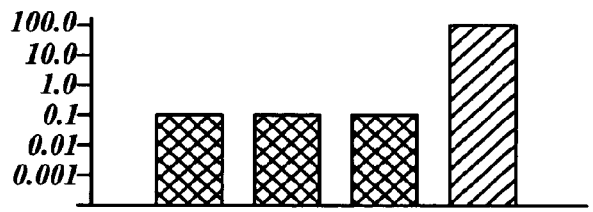

FIG. 15C shows the composition of the light transmitted by a camera filter, such as filter 119, for imaging the near-infrared reflectance image. In this configuration, the filter blocks the blue excitation light and red fluorescence light while transmitting near-infrared reflectance light in the wavelength range of 700-850 mm, or any desired subset of wavelengths in this range. The in-band transmission characteristics (in the wavelength range of 700-850 mm, or any desired subset of wavelengths in this range) are determined by the need to match the intensity of the reflected reference light projected onto the color image sensor to the requirements of the sensor, in combination with the characteristics of the light source filter described above. When used in a fluorescence endoscopy video system with the light source filter 76B described above and the dichroic mirror described below, the filter characteristics are such that any light outside of the wavelength range of 700-850 mm, or any desired subset of wavelengths in this range, contributes no more than 0.1% to the light transmitted by the filter.

Figure 15D:
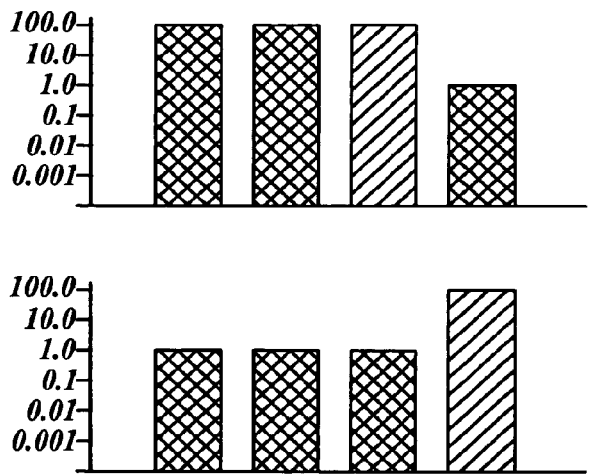

FIG. 15D shows the composition of the light transmitted by a dichroic mirror of the kind that may be employed in the dichroic splitter and filter assembly 120 to split the red fluorescence and near-infrared reflectance. The dichroic mirror preferably has a half-maximum transmission in the range of 690-710 nm. It may reflect the shorter wavelengths and transmit the longer wavelengths (long pass) or transmit shorter wavelengths and reflect longer wavelengths (short pass). As described above the dichroic splitter and filter assembly may incorporate the filters described in FIGS. 15B and 15C.

Figure 16A:
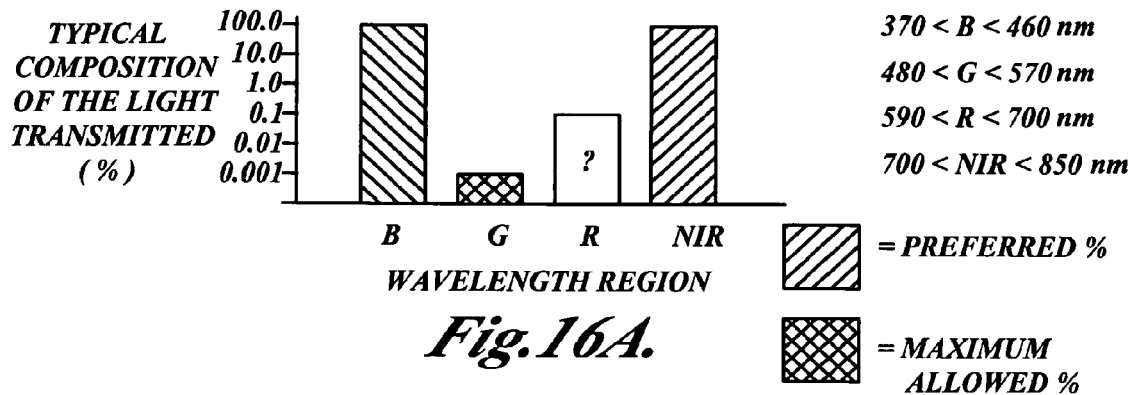
FIGS. 16A-16D are graphs illustrating presently preferred transmission characteristics of filters and dichroic splitters for fluorescence/reflectance imaging using green fluorescence light and near-infrared reflectance light.

FIGS. 16A-16D illustrate the preferred composition of the light transmitted by filters for a green fluorescence and near-infrared reflectance imaging mode. FIG. 16A illustrates the composition of the light transmitted by a light source filter which is used to produce excitation light, such as filter 76B described above. This filter transmits light in the blue wavelength range from 370-460 nm, or any subset of wavelengths in this range. It also transmits light in the near-infrared wavelength range of 700-850 nm, or any subset of wavelengths in this range. The light transmitted in the near-infrared wavelength range (or subset of that range) is adjusted, as part of the system design, to be an appropriate fraction of the light transmitted in the blue wavelength range to meet the need to match the intensity of the reflected reference light projected on the color image sensor to the requirements of the sensor, at the same time as maintaining sufficient fluorescence excitation. Of the light transmitted by this filter, less than 0.001% is in the green fluorescence imaging wavelength range of 480-570 nm (or whatever desired subset of this range is specified as the transmission range of the red fluorescence filter described below).

Figure 16B:
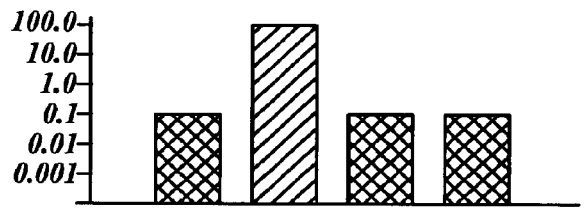

FIG. 16B shows the composition of the light transmitted by a camera filter, such as spectral filter 118, for imaging the green fluorescence image. In this configuration, the filter blocks the blue excitation light and near-infrared reflectance light while transmitting green fluorescence light in the wavelength range of 480-570 nm, or any subset of wavelengths in this range. When used in a fluorescence endoscopy video system with the light source filter 76B described above and the dichroic mirror described below, the filter characteristics are such that any light outside of the wavelength range of 480-570 nm, or any desired subset of wavelengths in this range, contributes no more than 0.1% to the light transmitted by the filter.

Figure 16C:
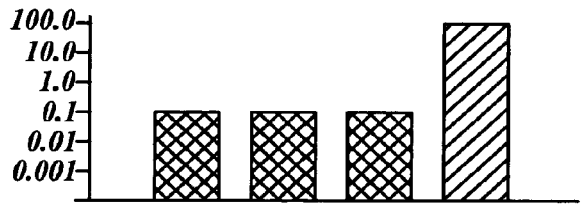

FIG. 16C shows the composition of the light transmitted by a camera filter, such as filter 119, for imaging the near-infrared reflectance image. In this configuration, the filter blocks the blue excitation light and green fluorescence light while transmitting near-infrared reflectance light in the wavelength range of 700-850 nm, or any desired subset of wavelengths in this range. The in-band transmission characteristics (in the wavelength range of 700-850 nm or any desired subset of wavelengths in this range) are determined by the need to match the intensity of the reflected reference light projected onto the color image sensor to the requirements of the sensor, in combination with the characteristics of the light source filter described above. When used in a fluorescence endoscopy video system with the light source filter 76B described above and the dichroic mirror described below, the filter characteristics are such that any light outside of the wavelength range of 700-850 nm, or any desired subset of wavelengths in this range, contributes no more than 0.1% to the light transmitted by the filter.

Figure 16D:
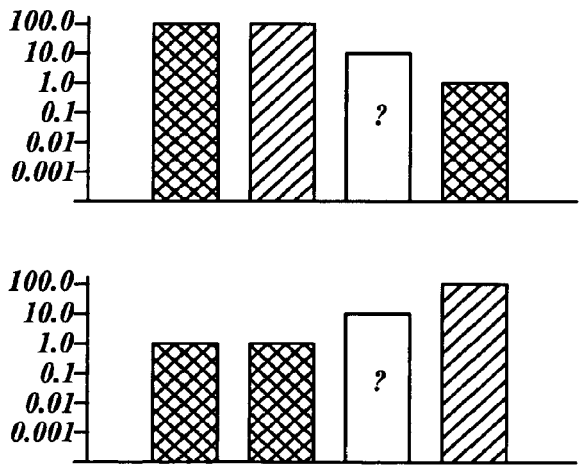

FIG. 16D shows the composition of the light transmitted by a dichroic mirror of the kind that may be employed in the dichroic splitter and filter assembly 120 to split the green fluorescence and near-infrared reflectance. The dichroic mirror preferably has a half-maximum transmission in the range of 590-660 nm. It may reflect the shorter wavelengths and transmit the longer wavelengths (long pass) or transmit shorter wavelengths and reflect longer wavelengths (short pass). As described above, the dichroic splitter and filter assembly may incorporate the filters described in FIGS. 16B and 16C.

FIGS. 17A-17D illustrate the preferred composition of the light transmitted by filters for use in a fluorescence endoscopy video system operating in fluorescence/fluorescence imaging mode wherein the tissue autofluorescence being excited and imaged is divided into two spectral bands.

Figure 17A:
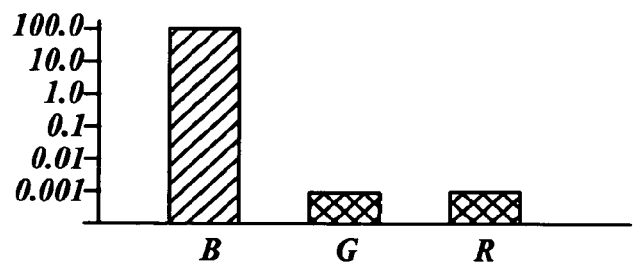
FIGS. 17A-17D are graphs showing presently preferred transmission characteristics of filters and dichroic splitters for use with fluorescence/fluorescence imaging.

FIG. 17A illustrates the composition of the light transmitted by a filter, such as filter 76C, which is used to produce excitation light in the system light source. This filter transmits light in the wavelength range from 370-460 nm, or any subset of wavelengths in this range. Of the light transmitted by this filter, less than 0.001% is in the fluorescence imaging band from 480-750 nm (or whatever desired subsets of this range are within the specified transmission range of the primary and reference fluorescence image filters described below).

Figure 17B:
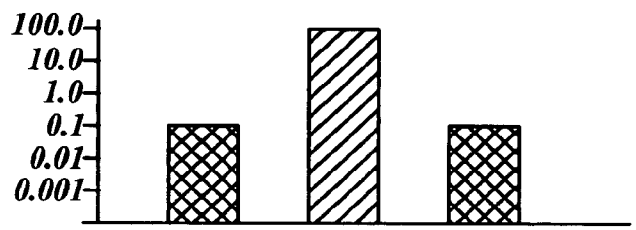

FIG. 17B shows the composition of the light transmitted by a camera filter, such as filter 118, for imaging the primary fluorescence image. In this configuration, the filter blocks excitation light and red fluorescence light while transmitting green fluorescence light in the wavelength range of 480-570 nm, or any subset of wavelengths in this range. When used in a fluorescence endoscopy video system with the light source filter 76C described above and the dichroic mirror described below, the filter characteristics are such that any light outside of the wavelength range of 480-570 nm, or any desired subset of wavelengths in this range, contributes no more than 0.1% to the light transmitted by the filter.

Figure 17C:
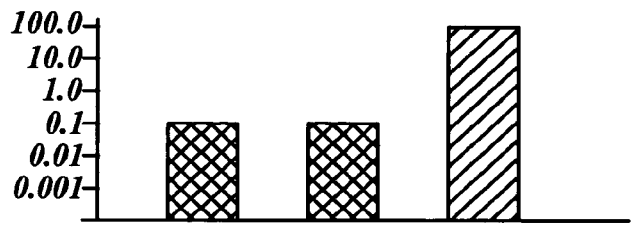

FIG. 17C shows the composition of the light transmitted by a camera filter for imaging the reference fluorescence image, such as filter 119. In this configuration, the filter blocks excitation light and green fluorescence light while transmitting red fluorescence light in the wavelength range of 590-750 nm, or any subset of wavelengths in this range. When used in a fluorescence endoscopy video system with the light source filter 76C described above and the dichroic mirror described below, the filter characteristics are such that any light outside of the wavelength range of 590-750 nm, or any desired subset of wavelengths in this range, contributes no more than 0.1% to the light transmitted by the filter.

Figure 17D:
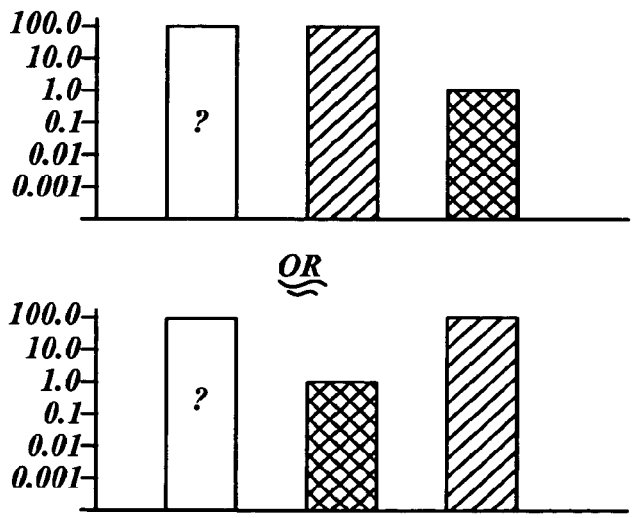

FIG. 17D shows the composition of the light transmitted by a dichroic mirror of the kind that may be employed in the dichroic splitter and filter assembly 120. The dichroic mirror preferably has a half-maximum transmission in the range of 570-590 nm. It may reflect the shorter wavelengths and transmit the longer wavelengths (long pass) or transmit shorter wavelengths and reflect longer wavelengths (short pass).

Figure 18:
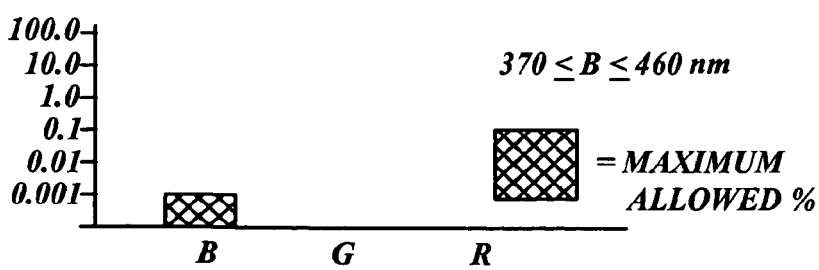
FIG. 18 is a graph illustrating presently preferred transmission characteristics of a blue blocking filter for fluorescence/reflectance or fluorescence/fluorescence imaging using a color image sensor with integrated selective filters.

FIG. 18 shows the composition of light transmitted by a filter 118' employed for blocking blue light in a camera such as that described in the fifth embodiment and shown in FIG. 10. The filter transmits light in the range 480-750 nm, or any subset of wavelengths of light in this range. Of the light transmitted by this filter, less than 0.001% is in the fluorescence excitation band from 370-460 nm (or whatever desired subset of this range is within the specified transmission range of the light source filters described above).

The fluorescence endoscopy video systems described in the above embodiments have been optimized for imaging endogenous tissue fluorescence. They are not limited to this application, however, and may also be used for photodynamic diagnosis (PDD) applications. As mentioned above, PDD applications utilize photoactive drugs that preferentially accumulate in tissues suspicious for early cancer. Since effective versions of such drugs are currently in development stages, this invention does not specify the filter characteristics that are optimized for such drugs. With the appropriate light source and camera filter combinations, however, a fluorescence endoscopy video system operating in either fluorescence/fluorescence or fluorescence/reflectance imaging mode as described herein may be used to image the fluorescence from such drugs.

Next, an aspect of a fluorescence endoscopy video system containing features to maintain a consistent imaging performance will be described. As mentioned earlier, the light signal response of a fluorescence endoscopy video system requires calibration. A feature to confirm and maintain this calibration is essential for clinically effective performance.

Figure 19:
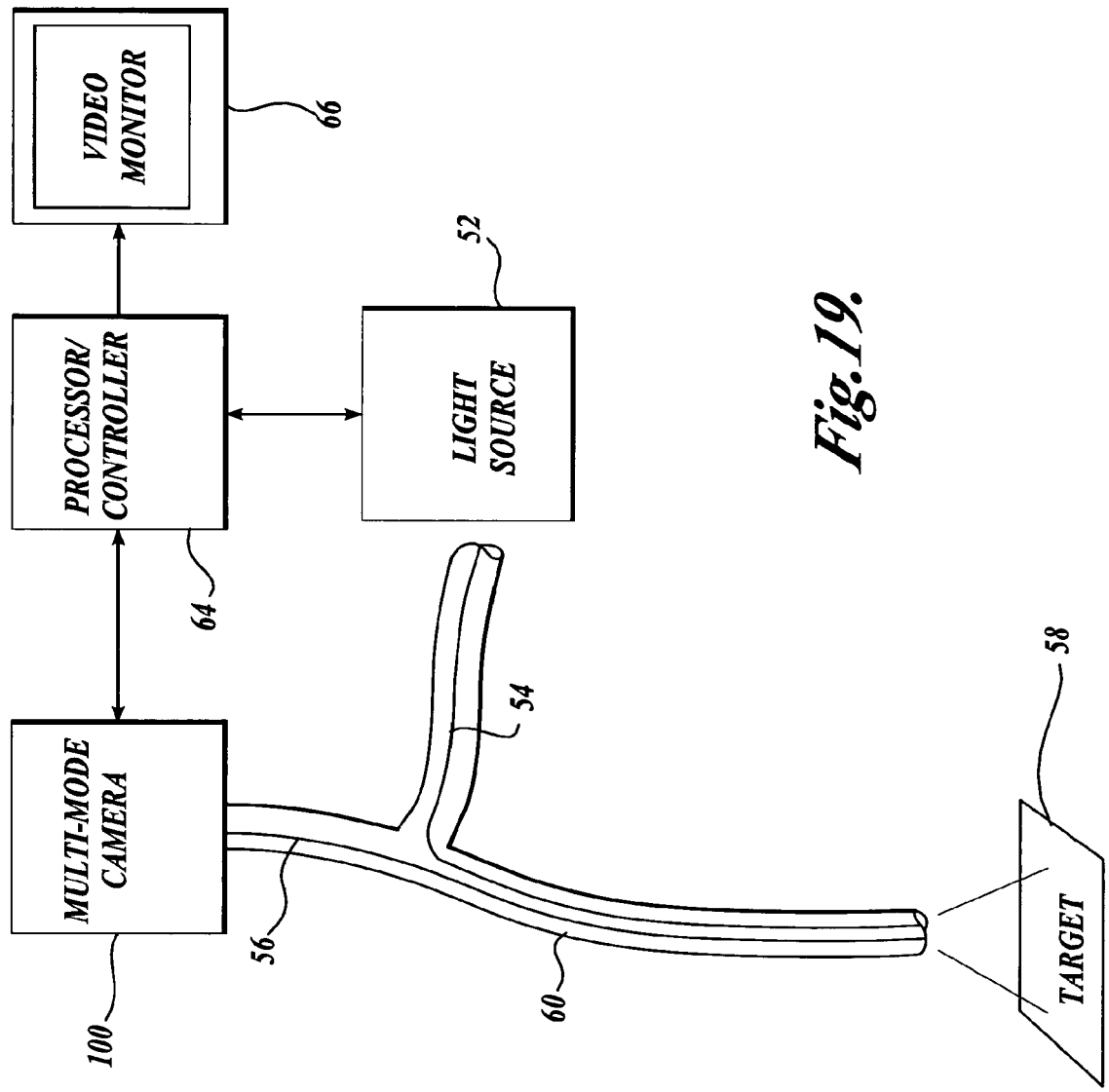
FIG. 19 is a block diagram of a system to perform color calibration of the fluorescence endoscopy video system according to another aspect of the present invention.

FIG. 19 shows a block diagram of the relevant system components involved in the process of self-calibration. Light from the light source 52 is supplied to an illumination guide 54 of an endoscope 60 and is directed to a fluorescence/reflectance target 59 with known fluorescence and reflectance properties. Depending on the imaging mode, fluorescence and reflectance light from the target 59 is collected and transmitted through an image guide 56 of the endoscope to the camera 100. The camera 100, operating in the fluorescence/reflectance or fluorescence/fluorescence mode, spectrally splits and transduces images into separate electrical signals, which are then digitized in the image processor/controller 64. The image processor/controller 64 quantifies the magnitude of these digitized image signals in terms of image gray levels. By using spatial and temporal averaging, the error in the quantified value of the signal response can be reduced to less than 1%. The image processor/controller 64 then compares the known properties of the target to the quantified signal response and adjusts the gain ratio described previously to the desired constant value. This adjustment compensates for variations in the signal path between the target 59 and image processor/controller 64, due to factors such as variations in transmission properties of different endoscopes being used with the system and changes in the signal response of the system with age. Such self-calibration ensures that the gain ratio is set to a value such that tissue suspicious for early cancer in a fluorescence image will appear as a distinctly different color than normal tissue. This self-calibration could be carried out before every endoscopy.

Although this method is similar to existing methods used to adjust the color response of standard camera systems, such a technique has not been previously applied to multispectral fluorescence or fluorescence/reflectance endoscopy. The method uses a reference target 59 that provides suitable known fluorescence and reflectance response to the light from the light source.

Any suitable object with appropriate fluorescence and reflectance properties can be used as a reference target. For example, such a reference target 59 can be made by mixing a fluorescent dye(s) and light scattering materials into a liquid. The liquid used may be a solute (such as methanol) enclosed in a container with an optical window, or alternatively may be a liquid which hardens to form a solid (such as an epoxy). The dye(s) used must be appropriately soluble in the liquid utilized. The fluorescence spectrum and brightness of the target 59 is controlled by the choice and concentration of the fluorescence dye (or dyes) contained in the target. The fluorescent dye(s) must be chosen such that the light emitted by the light source 52 excites fluorescence light in the green and/or red wave bands defined by the camera filters described above that correspond to a particular imaging mode. The fluorescent dye(s) must also be stable with time and not undergo significant photobleaching. One such fluorescent dye is Coumarin #540A. The concentration of the fluorescence dye in the target is chosen such that the emitted fluorescence light produces mid-range signal amplitudes at or near a particular clinically used gain setting.

The reflectance property of the target is controlled by the type and concentration of scattering material added to the target. The type of scattering material is chosen for good reflectivity of the reference light in the wavebands defined by the camera filters described above that correspond to a particular fluorescence/reflectance imaging mode. The concentration of the scattering material in the target is chosen such that the reflected reference light produces mid-range signal amplitudes at or near a particular clinically used gain setting.

Once a reference target having the appropriate fluorescence and reflectance properties has been made, these properties are verified and validated using fluorescence spectroscopy and reflectance spectroscopy.

Next, another aspect of a fluorescence endoscopy video system will be described in which the perceived color contrast between normal tissue and tissue suspicious for early cancer is enhanced by means of a contrast enhancement algorithm that is applied to the digitized image signals in the image processor/controller 64.

In fluorescence endoscopy video images, the contrast between normal tissue and tissue suspicious for early cancer is typically the result of a reduction in the fluorescence signal associated with the disease, which is not matched by a corresponding reduction in the reference signal. Such image areas are therefore characterized by a combination of reduced image brightness and altered color. In such image areas of relative darkness, the color difference between suspected lesions and the surrounding normal tissue can be difficult to discern. To aid physicians in detecting these subtle color changes, the present invention also includes a method of enhancing the contrast between normal and tissue suspicious for early cancer. This method consists of a software algorithm that is applied to the digitized fluorescence/reflectance (or fluorescence/fluorescence) image signals by the image processor/controller 64, and may be utilized in all embodiments of a fluorescence endoscopy video system described previously.

The contrast enhancement method alters the color and intensity of a pixel in the displayed fluorescence video image as a function of the pixel characteristics and, possibly, as a function of the neighboring pixel characteristics. The algorithm consists of a number of elements. Firstly, it characterizes the image on a pixel-by pixel-basis by determining properties such as the ratio of the intensity of the reference image to the intensity of the fluorescence image. The algorithm may also characterize the image by other properties, such as the spatial texture associated with the color in an area containing the pixel of interest. In the second step, the algorithm applies a test to the pixel property values. This test will determine whether the pixel property values fall within a certain specified range. Finally, a function, whose value depends on the results of the test, is applied to change the pixel display properties. The function changes the properties of those pixels whose characterized property values fall within a certain range. These pixels will have their properties changed in such a way that, in the displayed video image, they are more easily distinguished from those pixels that do not have characterized property values that fall within the specified range. By choosing a test that selects pixel property values corresponding to early cancer, the contrast between normal tissue and tissue suggestive for early cancer can be enhanced.

The general algorithm will now be described in more detail. The first step is to quantify pixel properties. Given that the fluorescence from tissue areas with early cancer typically exhibits both reduced brightness and altered color, intensity and color are the pixel properties that can be used to identify such an area. In a dual image sensing system, such as those described in the aforementioned embodiments, the algorithm may measure the intensity of the fluorescence image, the intensity of the reference image (reflectance or fluorescence), or some combination of these. Since the reference and fluorescence images are acquired in different parts (wavebands) of the fluorescence spectrum, the color of a pixel can be characterized by the ratio of the intensity of the reference image to the intensity of the fluorescence image.

Other pixel properties may also be useful in characterizing tissues suspicious for early cancer. The spatial texture of the color may be such a property. One means of characterizing the color texture is to calculate the mean and standard deviation of the ratio of the intensity of the reference image to the intensity of the fluorescence image for pixels in an area of defined size containing the pixel of interest. The standard deviation of this ratio provides a measure of the color texture, which can be associated with the pixel of interest. Another way to characterize the color texture is to calculate the two-dimensional Fourier transform of the color ratio in an area of defined size containing the pixel of interest. Other pixel or pixel neighborhood properties that uniquely characterize tissue suspicious for early cancer can be quantified using similar techniques.

The next step in the algorithm is to apply a test to the values of the pixel properties. Such a test can be single dimensional or multidimensional. For example, such a test may be based solely on the value of one pixel property (e.g., whether or not the ratio of the reference image intensity to the fluorescence image intensity falls within a given range) or it may be based on a combination of the values of several pixel properties (e.g., whether or not the ratio falls with a given range and the reference intensity falls within a defined range, and the color texture falls within a given range).

Following the test, a function, which depends on the result of the test, is applied to the properties of the pixel. Such a function changes one or more pixel properties, based on the outcome of the test. The function can operate on both the fluorescence and reference image components of the displayed video image or on only one of them. The function can be linear or nonlinear.

Three embodiments of contrast enhancement algorithms for a fluorescence endoscopy system, of the type described above, will now be illustrated.

Figure 20:
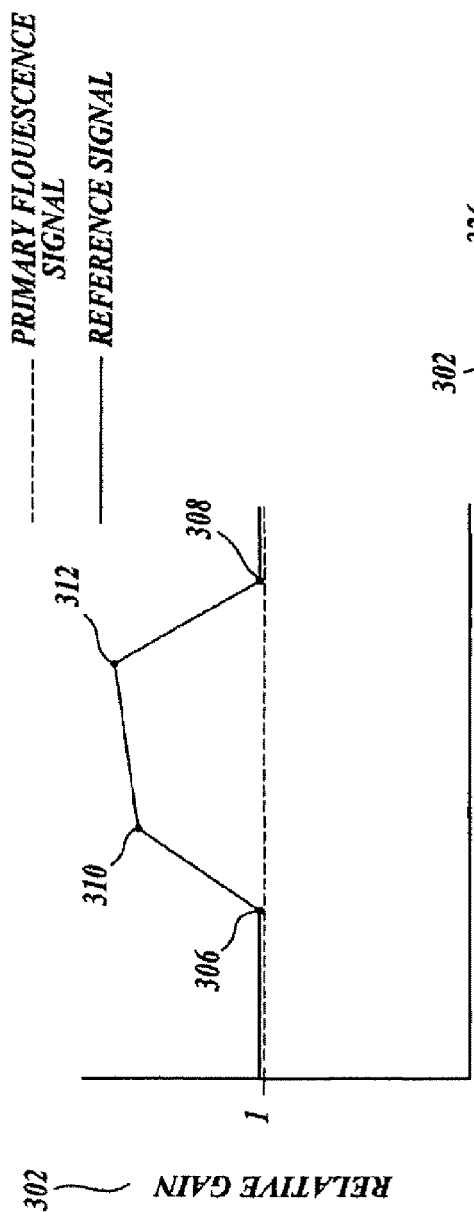
FIGS. 20-22 are graphs showing contrast enhancement tests and functions that can be used to highlight potentially cancerous tissue in accordance with another aspect of the present invention.

The first embodiment of a contrast enhancement algorithm for a fluorescence endoscopy system is best described by means of FIG. 20. This figure illustrates the test and corresponding function applied to the properties of each pixel. The vertical axis in the figure represents the function 302, a relative gain, to be applied to the digitized image signals. A separate gain is applied to the primary fluorescence image signal and the reference (reflectance or fluorescence) signal. The horizontal axis represents the value of a pixel property 304. In this embodiment the pixel property 304 is the ratio of the reference (reflectance or fluorescence) image signal (intensity) to the primary fluorescence image signal.

In the example shown in FIG. 20, the gain applied to the primary fluorescence image signal is unity. The gain applied to the reference (reflectance or fluorescence) image signal is increased when the ratio falls within the range defined by break points 306 and 308. As shown in the figure, the gain function applied to the reference (reflectance or fluorescence) image signal has a constant value up to a break point 302. This gain then increases linearly to a break point 310, continues linearly to another break point 312, and decreases linearly to break point 308, beyond which it remains constant. The position of the break points on the horizontal axis, and the gain function value at all break points, can be adjusted by the operator of the fluorescence endoscopy video system.

It has been determined that, if a fluorescence endoscopy video system is appropriately calibrated as described above, the fluorescence and reflectance image signals from tissues suspicious for early cancer will consistently and uniquely produce ratio values within a specific range. The operator may select gain break points 306 and 308 to be positioned at the extremes of this range and thereby apply a gain to the reference reflectance (or fluorescence) signal over the entire range of ratio values that correspond to tissue suspicious for early cancer.

As described above, the processed primary fluorescence image signal and the processed reference (reflectance or fluorescence) signal are input to color video monitor 66 as different color components of a single superimposed image. By selective application of the gain function to the reference (reflectance or fluorescence) signal as described, its contribution to the color of the superimposed image is increased and the color contrast between image pixels of normal tissue and image pixels of tissue suspicious for early cancer is enhanced.

Note that if the piecewise linear function illustrated in FIG. 20 is replaced by any similar function, not necessarily linear, comparable contrast enhancement can be obtained.

A second embodiment of the contrast enhancement algorithm will now be described. All points of similarity with the first embodiment will be assumed understood and only points that differ will be described.

In the second embodiment of a contrast enhancement algorithm for a fluorescence endoscopy system, in addition to the test and function operating on pixel properties described in the first embodiment, a second additional test and function is applied. The additional test element and function is illustrated by means of FIG. 21. The vertical axis in the figure represents the function, a relative gain 322, to be applied to the digitized image signals. A separate gain function is applied to the primary fluorescence image signal and the reference (reflectance or fluorescence) signal. The horizontal axis represents the value of a pixel property 324, which is either the intensity of the primary fluorescence image signal, or the intensity of the reference (reflectance or fluorescence) signal, or a two-dimensional combination of these.

Figure 21:
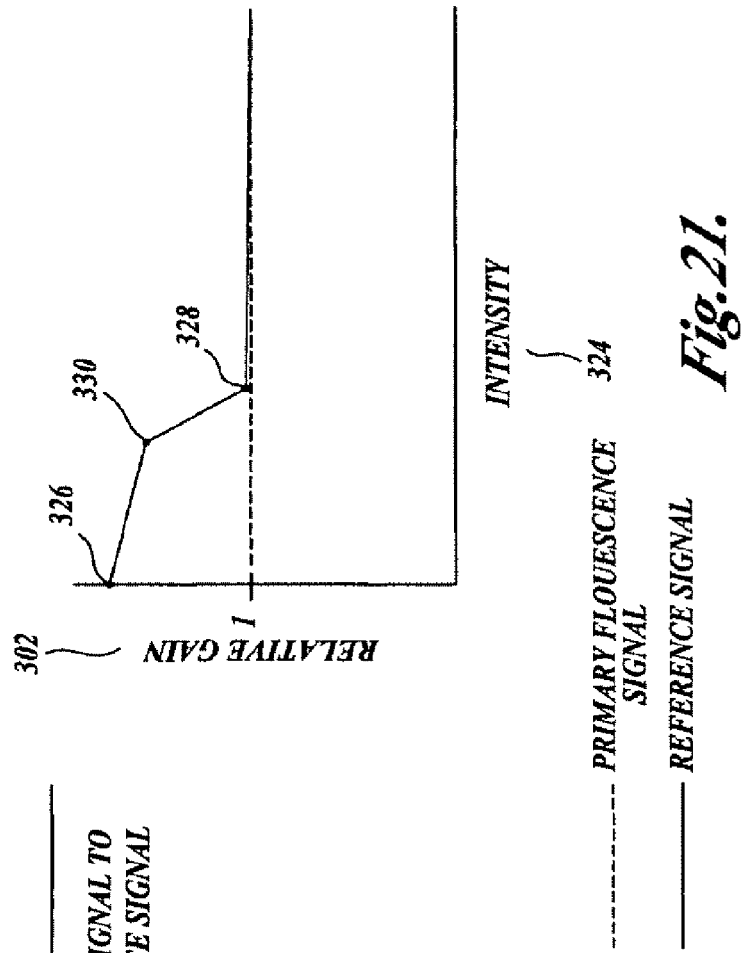

The gain function applied to the fluorescence image signal is unity. The gain applied to the reference image signal decreases linearly above breakpoint 326 to breakpoint 330. It then decreases linearly beyond break point 330 to break point 328. Beyond break point 328 the gain function is constant. In this embodiment, the tests and functions illustrated by both FIGS. 20 and 21 are applied sequentially with the result that two or more sets of gain factors are applied. The net result is a modification of the intensity value of the pixel of interest by two or more multiplicative factors applied following two or more separate tests. This embodiment is an example of a multiparameter test discussed previously. As in the first embodiment, the operator may select the gain factor break points shown in FIG. 20. The operator may also select the gain factor break points 326, 328, and 330, along with their associated gain values. Also as described in the first embodiment, if the piecewise linear functions illustrated in FIGS. 20 and 21 are replaced by any similar functions, not necessarily linear, comparable contrast enhancement can be obtained.

A third embodiment of the contrast enhancement algorithm will now be described. All points of similarity with the first embodiment will be assumed understood and only points that differ will be described.

Figure 22:
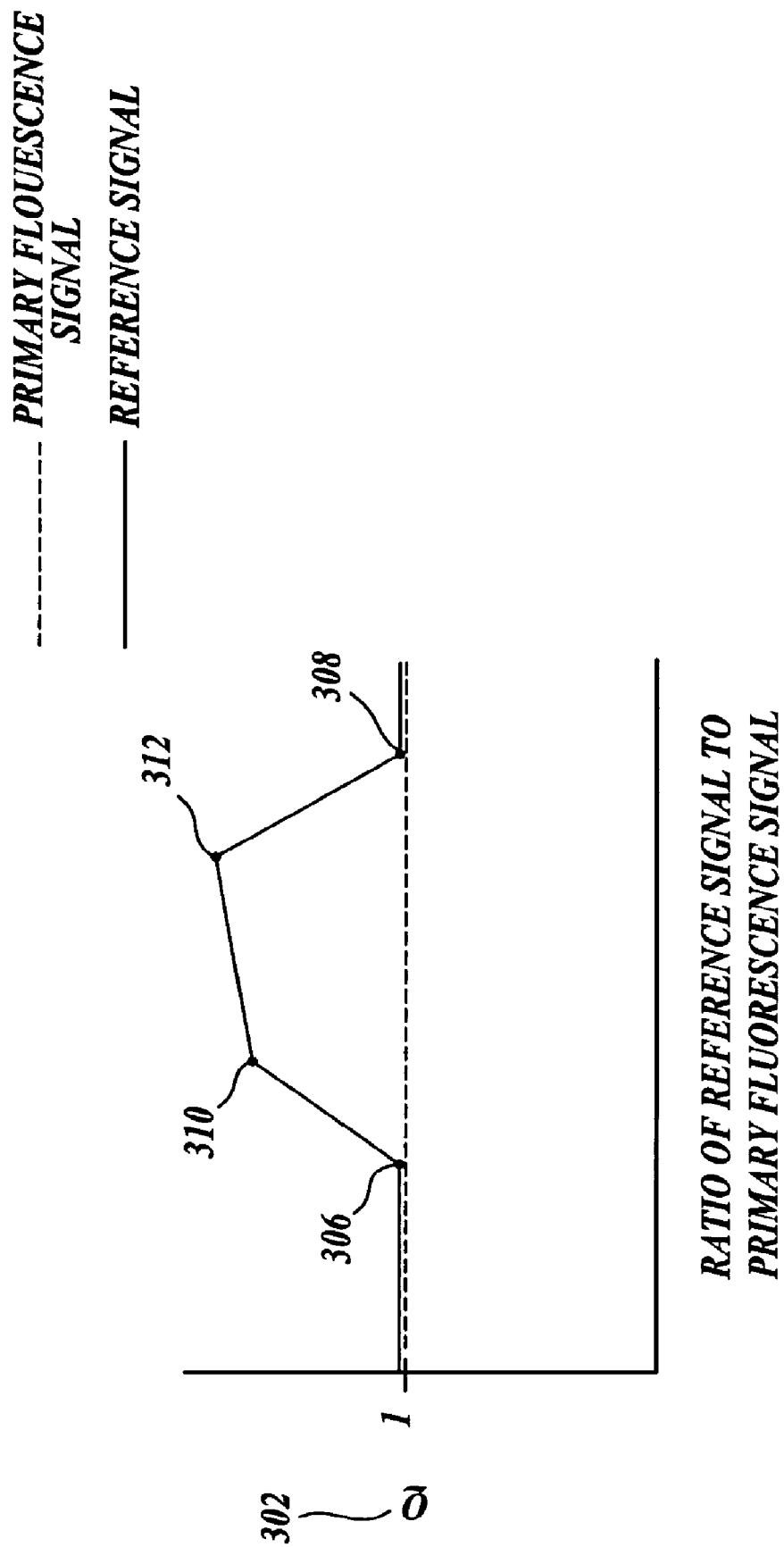

The third embodiment of a contrast enhancement algorithm for a fluorescence endoscopy system is similar to the first embodiment, except that the linear gain function utilized in the first embodiment is replaced by a nonlinear function. FIG. 22 illustrates the test applied to the properties of each pixel. This figure is similar to FIG. 20, except that instead of representing gain, the vertical axis represents an intermediate parameter, Q 340. The horizontal axis represents the value of a pixel property 304. In this embodiment the pixel property 304 is the ratio of the reference (reflectance or fluorescence) image signal value to the primary fluorescence image signal value for a given image pixel. The parameter Q is used to calculate the gain to be applied at each pixel via Equation 3

$$F(r_{in}) = \left(\frac{r_{in}}{r_{max}}\right)^{\frac{1}{Q}-1} \quad (3)$$

where $F(r_{in})$ is the gain, $r_{in}$ is the image signal value, and $r_{max}$ is the maximum possible image signal value.

In this embodiment, the value of Q for the primary fluorescence image signal is unity for all (reference image signal value to fluorescence image signal) ratio values. As a result, the gain calculated from the equation above and applied to the primary fluorescence image signal is also unity.

The value of Q for the reference image signal increases when the (reference image signal value to fluorescence image signal) ratio falls within the range defined by break points 306 and 308. As shown in the figure, the value of Q has a constant value up to a break point 302, before increasing linearly to a break point 310, continuing linearly to another break point 312, and decreasing linearly to break point 308, beyond which it remains constant. The position of the break points on the horizontal axis, and the gain factors at all break points, can be adjusted by the operator of the fluorescence endoscopy video system.

Using the value of Q, the gain function is calculated for each pixel of the reference image signal. If the value of Q is greater than one, the value of the reference image signal to which the gain is being applied will increase nonlinearly with increasing values of Q. The gain applied to the reference image signal is larger for lower reference image signal values. The net result of this test and function is that the resulting contrast enhancement depends on both the ratio of the reference image signal value to the primary fluorescence image signal value and the reference image signal value.

If the piecewise linear function illustrated in FIG. 22 is replaced by any similar function, not necessarily linear, comparable contrast enhancement can be obtained.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privelage is claimed are defined as follows:

1. A fluorescence endoscopy video system including:
   a multimode light source for producing white light, fluorescence excitation light or fluorescence excitation light and reference reflectance light;
   an endoscope for directing the light from the light source into a patient to illuminate a tissue sample and to collect reflected light and fluorescence light emitted from the tissue;
   a camera positioned to receive the light collected by the endoscope, the camera including:
   a high sensitivity color image sensor;
   a beam splitter for splitting the light received from the endoscope into at least two beams and one or more optical imaging components that, in combination, project images onto separate imaging areas disposed in the same image plane of the high sensitivity color image sensor; and
   one or more filters positioned in front of the separate imaging areas of the high sensitivity color image sensor;

a light source filter positioned in the light path of the light source that simultaneously transmits the fluorescence excitation light and an amount of reference reflectance light not in a fluorescence detection wavelength band, wherein the amount of reference reflectance light transmitted is a fraction of the fluorescence excitation light such that the intensity of the reflected reference light projected onto the high sensitivity color image sensor matches the intensity of fluorescence also projected onto the high sensitivity color image sensor and wherein the intensities of the projected fluorescence and reflected reference light also match a light sensitivity of the sensor, and wherein the light source filter blocks light from the light source at wavelength in the fluorescence detection wavelength band from reaching the high sensitivity color image sensor to the extent that the light received by the high sensitivity color image sensor is substantially composed of fluorescence emitted from the tissue and minimally composed of light originating from the light source;

an image processor for digitizing, processing and encoding image signals from the separate imaging areas of the high sensitivity color image sensor; and a video monitor for displaying corresponding images.

2. The system of claim 1, wherein the beam splitter comprises one or more dichroic plates or prisms, or both, with each plate or prism having at least one partially reflecting surface and each prism having in addition at least one reflecting surface arranged to divide incoming light into at least two separate beams having substantially identical optical path lengths.

3. The system of claim 1, wherein one filter in front of one imaging area of the high sensitivity color image sensor blocks reflected excitation light and reference light, and transmits fluorescence light to the extent that the light received by the high sensitivity color image sensor is substantially composed of fluorescence emitted from the tissue and minimally composed of light originating from the light source, the amount of reference reflectance light transmitted by the filter being such that the intensity of the reference light projected onto the color image sensor matches the requirements of the sensor, and a second filter in front of a second imaging area of the high sensitivity color image sensor blocks reflected excitation light and transmits reference reflectance light to the extent that the light received by the second imaging area of the high sensitivity color image sensor is substantially composed of reference reflectance light and minimally composed of excitation light, the amount of reference reflectance light transmitted by the second filter being such that the intensity of the reflected reference light passing through the second filter and projected onto the high sensitivity color image sensor matches the intensity of the fluorescence light projected onto the first area of the high sensitivity color image sensor and matches the requirements of the sensor.

4. The system of claim 3, wherein the fluorescence, transmitted by at least one filter in front of the high sensitivity color image sensor, is green light.

5. The system of claim 4, wherein the reference reflectance light, not in the detected fluorescence band, transmitted by the light source filter is red light.

6. The system of claim 4, wherein the reference reflectance light, not in the detected fluorescence band, transmitted by the light source filter is near-infrared light.

7. The system of claim 4, wherein the reference reflectance light, not in the detected fluorescence band, transmitted by the light source filter is blue light.

8. The system of claim 3, wherein the fluorescence, transmitted by at least one filter in front of the high sensitivity color image sensor, is red light.

9. The system of claim 8, wherein the reference reflectance light, not in the detected fluorescence band, transmitted by the light source filter is green light.

10. The system of claim 8, wherein the reference reflectance light, not in the detected fluorescence band, transmitted by the light source filter is near-infrared light.

11. The system of claim 8, wherein the reference reflectance light, not in the detected fluorescence band, transmitted by the light source filter is blue light.

12. A fluorescence endoscopy video system comprising:

a multimode light source for producing white light, fluorescence excitation light or fluorescence excitation light and reference reflectance light;

an endoscope for directing the light from the light source into a patient to illuminate a tissue sample and to collect reflected light and fluorescence light emitted from the tissue;

a camera positioned to receive the light collected by the endoscope, the camera including:
a high sensitivity color image sensor;
a beam splitter for splitter the light received from the endoscope into at least two beams and one or more optical imaging components that, in combination, project images onto separate imaging areas disposed in the same image plane of the high sensitivity color image sensor; and one or more filters positioned in front of the separate imaging areas of the high sensitivity color image sensor;

wherein one of the filters in front of one imaging area of the high sensitivity color image sensor blocks reflected excitation light and transmits fluorescence light in a green wavelength band to the extent that the light received in the first area of the high sensitivity color image sensor is substantially composed of fluorescence emitted from tissue in a green wavelength band and minimally composed of light originating from the light source, and a second filter in front of a second imaging area of the high sensitivity color image sensor blocks reflected excitation light and transmits fluorescence light in a red wavelength band to the extent that the light received in the second area of the high sensitivity color image sensor is substantially composed of light resulting from tissue fluorescence in a red wavelength band and minimally composed of light originating from the light source a light source filter positioned in the light oath of the light source that transmits the fluorescence excitation light and blocks light, not at wavelengths in the detected fluorescence bands, from reaching the imaging areas of the high sensitivity color image sensor to the extent that the light received by the sensor is substantially composed of light resulting from fluorescence emitted from tissue and minimally composed of light originating from the light source, an image processor for digitizing, processing and encoding image signals from the separate imaging areas of the high sensitivity color image sensor; and a video monitor for displaying corresponding images.

13. The system of claim 12, wherein the processor/controller includes a memory device that stores a sequence of instructions that cause the processor/controller to adjust an intensity of the fluorescence or reference image signal on a pixel by pixel basis as a function of an analysis of the signals received from the different image areas of the high sensitivity color image sensor, and then encodes the adjusted image signals received from the sensors as a video signal for displaying corresponding images on the video monitor.

14. The system of claim 13, wherein the analysis of the digitized image signals that the processor/controller carries out utilizes a ratio of an intensity of the reference reflectance light and the fluorescence light received from the tissue.

15. The system of claim 13, wherein the analysis of the digitized image signals that the processor/controller carries out utilizes an intensity of pixels that neighbor the one or more pixels and adjusts the processed image signals based on the neighboring pixel intensities.

* * * * *